US012611206B2

(12) United States Patent
Green et al.

(10) Patent No.: US 12,611,206 B2
(45) Date of Patent: Apr. 28, 2026

(54) POSITIVE DISPLACEMENT CLOSURE DEVICES AND METHODS

(71) Applicant: Transluminal Technologies LLC, Syracuse, NY (US)

(72) Inventors: Stephen M. Green, Syracuse, NY (US); Ronald P. Caputo, Manlius, NY (US); John M. Kirwan, Wilbraham, MA (US)

(73) Assignee: Transradial Technologies, Inc., Syracuse, NY (US)

( * ) Notice: Subject to any disclaimer, the term of this patent is extended or adjusted under 35 U.S.C. 154(b) by 0 days.

(21) Appl. No.: 17/883,291

(22) Filed: Aug. 8, 2022

(65) Prior Publication Data

US 2023/0041471 A1     Feb. 9, 2023

Related U.S. Application Data

(60) Provisional application No. 63/230,236, filed on Aug. 6, 2021.

(51) Int. Cl.
A61B 17/132     (2006.01)
A61B 17/00      (2006.01)

(52) U.S. Cl.
CPC ............................... A61B 17/0057 (2013.01); *A61B 2017/00561* (2013.01); *A61B 2017/00646* (2013.01); *A61B 2017/0065* (2013.01); *A61B 17/1325* (2013.01)

(58) Field of Classification Search
CPC ...... A61B 17/0057; A61B 2017/00646; A61B 2017/00561; A61B 17/1325; A61B 2017/0065
See application file for complete search history.

(56) References Cited

U.S. PATENT DOCUMENTS

| | | | | |
|---|---|---|---|---|
| 2004/0030304 A1* | 2/2004 | Hunt | ..................... | A61L 15/425 |
| | | | | 604/317 |
| 2004/0243073 A1* | 12/2004 | Lockwood | .............. | A61M 1/85 |
| | | | | 602/41 |
| 2005/0165445 A1* | 7/2005 | Buckman | ................ | A61F 13/00 |
| | | | | 606/213 |
| 2011/0066178 A1* | 3/2011 | Blin | ........................ | A61M 1/08 |
| | | | | 606/201 |
| 2015/0216733 A1* | 8/2015 | Allen | .................. | A61F 13/5376 |
| | | | | 604/319 |
| 2020/0029946 A1* | 1/2020 | Green | .................... | A61B 17/08 |

* cited by examiner

*Primary Examiner* — Jing Rui Ou
(74) *Attorney, Agent, or Firm* — Hubert W. Pfabe

(57)     ABSTRACT

Devices and methods for creating hemostasis at a subcutaneous vascular puncture are disclosed. The methods and devices may be used to close vascular punctures following trans-radial arterial procedures, e.g., catheterization and percutaneous coronary intervention. The devices may include a housing defining a suction chamber and an anvil disposed within the suction chamber and adhesively attached to the limb of a patient such that the apparatus creates a pulling force as well as a pushing force on the patient's skin, subcutaneous tissue, and artery. Alternatively, the pulling force and pushing force may be accomplished be mechanical means.

10 Claims, 18 Drawing Sheets

322

370, 371

321

323

328

324

POSITIVE DISPLACEMENT CLOSURE DEVICES AND METHODS

This application claims priority to U.S. Provisional Patent Application No. 63/230,236 filed on Aug. 6, 2021, the disclosure of which is incorporated herein in its entirety.

BACKGROUND

The present disclosure relates to medical devices, and more particularly, to a vascular puncture hemostasis apparatus following trans-radial arterial procedures.

SUMMARY

The present disclosure relates to medical devices, and more particularly, to a vascular puncture hemostasis apparatus used following trans-radial arterial procedures. More particularly, the present disclosure relates to an arteriotomy closure device, associated instrumentation and equipment, and associated methods of use.

Various medical procedures, particularly interventional cardiology procedures, involve accessing a corporeal blood vessel through a percutaneous sheath. Insertion of the sheath necessarily requires an opening, or puncture wound, in the blood vessel so that a medical procedure can be performed through the sheath. After the medical procedure has been completed, or the use of the sheath is no longer beneficial, the sheath is removed from the blood vessel and the access hole in the blood vessel must be closed to enable or aid in cessation of bleeding from the blood vessel.

As an alternative to the historically standard access to the vasculature via the femoral artery in a patient's groin, access via an artery in a patient's wrist (i.e., either the radial artery or the ulnar artery) has gained recent popularity. This is particularly due to lessened post-procedure access site bleeding complications. The standard means for inducing post-procedure hemostasis of either a radial artery or an ulnar artery is to apply direct pressure, such as in a relatively/relationally downward direction, to the patient's wrist proximate of the subcutaneous sheath entry site, or arteriotomy. Several devices have been introduced into the device market which aid in applying such direct pressure to a patient's wrist. These hemostasis devices are frequently composed of a wrist band with a means for applying direct contact pressure on the patient's inside wrist skin surface approximate to the subcutaneous vessel's puncture wound. In order for such devices to effectively create hemostasis at the artery's puncture site, or arteriotomy, they must necessarily compress the soft tissue overlying the blood vessel. Such wrist band type devices may incorporate an inflatable balloon element for further focusing the direct pressure at a position on the patient's wrist overlying the arterial puncture.

By design, these inflatable balloon compression devices apply pressure to the patient's wrist, spread over a relatively small area with enough inward force to effect cessation of bleeding from the arteriotomy. Such application of pressure to the wrist surface, however, may result, in certain instances, in flattening, or collapsing, of the lumen of the subcutaneous artery. When the arterial lumen collapses, the blood flow path through the artery is narrowed. This can result in arterial occlusion through a variety of mechanisms—particularly when there is complete cessation of arterial flow during compression. Such occlusion of a radial artery and the resulting non-patency can create reduced blood flow to the patient's hand, as well as render the radial artery unusable for future percutaneous procedures. Arterial occlusion occurs in approximately 5%-12% of patients undergoing procedures through the radial artery approach and therefore relates to a substantial patient population, particularly in high volume hospitals.

In addition to the probability of arterial occlusion following application of direct pressure at the access site, there are also patient complaints of access site pain and discomfort owing to the prolonged clamping and direct pressure to the inside wrist surface. The pressure applied to the wrist area by a radial compression band, by design, is diffuse in nature. This can lead to venous congestion of the hand and has been reported by patients as painful.

The pain experienced by patients undergoing radial compression can be unpleasant. The arteriotomy closure device disclosed herein offers a method for facilitating hemostasis at a radial or ulnar artery puncture while avoiding the deleterious conditions that can result including pain, discomfort and arterial occlusion during administration of direct pressure at the access site.

The arteriotomy closure device disclosed herein creates an upward pulling force, or positive displacement, on the skin, subcutaneous tissue (the connective tissue) and the artery via a low modulus/low durometer securement band which is adhesively attached to the patient's skin via a "peel and stick" underside. The force is referred to herein as "upward", though it should be understood herein and hereafter that "upward" is being used in the interest of simplicity, and the force is directed away from the patient, such as to be directed from proximal to the area of the arteriotomy towards a proximal relative location relative to the user of the device, and distal from the patient. Similarly and conversely, "downward" is used herein to refer to distal from the user of the arteriotomy device and towards a patient. When an upward pulling force is applied to the securement band, so too is the upward force transmitted to the skin, subcutaneous tissue and the artery. The direction of the upward pulling force is distinctly opposite of compression device, which applies a downward pushing force on the skin, subcutaneous tissue and the artery.

The arteriotomy closure device may utilize multiple mechanisms for applying the upward pulling force, or positive (upward) displacement to the securement band, and thereby to the skin, subcutaneous tissue and artery. Various means of creating or utilizing a positive, or upward, or distal to the patient or arteriotomy site, force are disclosed herein, and it should be understood that minor variations to such creation or utilization are also incorporated in this disclosure, as may be understood by one with knowledge in the art.

The arteriotomy closure device disclosed herein may use a suction force applied to the top surface of the low modulus/low durometer securement band which is adhesively attached to the skin surface at its bottom surface. A suction force may be understood to include a low pressure localized area, such as within a portion of the arteriotomy closure device, relative to surrounding pressures. The suction force creates extension or localized distortion of movement of the compliant band, such that the skin is not exposed to the presence of negative pressure, or suction, but the adhesive connection of the band to the skin provides an upward pulling force on the skin and the underlying connective tissues, and the artery. The disclosed methods include pulling the artery via its surrounding soft tissue against a stable, stationary platform such as an anvil.

Another embodiment is disclosed whereby the upward force and resulting positive (upward) displacement to the securement band, and thereby to the skin, subcutaneous tissue and artery is provided by a mechanical apparatus which is adhesively bonded to the top surface of the band, such that when the upward pulling force is applied to the elastic band, so too is the upward force transmitted to the skin, subcutaneous tissue and the artery. Once displaced in an upward direction, the skin, along with the subcutaneous tissue and artery are pulled upward against a stable, stationary platform such as an anvil.

As determined empirically via direct ultrasound visualization, when upward force is applied to the skin surface, the underlying artery is drawn in an upward direction while maintaining the natural substantially cylindrical cross-sectional geometry of the artery's lumen without collapsing the lumen and resultantly potentially impeding the flow of blood. By drawing the artery and its surrounding subcutaneous connective tissue in a direction closer to the skin (and thereby compressing the soft subcutaneous tissue overlying the artery), it is then possible to apply a more concentrated pressure point (or line of pressure) directed specifically at the arteriotomy and with a significantly lower net inward force, thus avoiding overall collapse of the arterial lumen. It is further an assertion of this method that it is considerably more comfortable for the patient than the direct compression technique.

One embodiment of a closure device includes a suction chamber which is adhesively bonded to the top surface of a low modulus/low durometer securement band whereby the securement band is a gas-impermeable membrane. At this interface, the integrity of the adhesive bond is substantially leak-proof or otherwise is configured to substantially provide a vapor and/or pressure barrier when a negative gauge pressure is applied to the suction chamber.

The bottom surface of the low modulus/low durometer securement band may utilize a "peel and stick" adhesive which is applied to the patient's wrist directly overlying the arterial puncture site. The adhesive of the "peel and stick" bottom surface of the band may provide an adequate connection to the skin such that when suction is applied to the suction chamber, the upward pulling force provided by suction concomitantly applies an upward pulling force on the skin, subcutaneous tissue and artery.

Further, the low modulus/low durometer securement band with a "peel and stick" skin-contacting bottom surface may insure that the band and the suction chamber will not dislodge during the duration of application to the patient's wrist as is frequently the case with compression-type devices or may otherwise impede such dislodgement.

The suction chamber may also include a stationary, distally protruding counter force member that provides and maintains a localized counter force against the patient's skin (directly overlying and/or approximate to the arteriotomy) during which time a suction force or negative gauge pressure is applied to the suction chamber. The low modulus/low durometer securement band may be locally drawn into the distal end of the suction chamber (i.e., puckered in an upward direction), as is the skin via the adhesive attachment to the securement band, and is approximated against the protruding anvil. Along with the skin being distended into the suction chamber, so too may the underlying tissue (including the artery) be drawn in an upward, or distended, position. While the suction force is being applied to the suction chamber, the stationary protruding counter force member may exert a localized counter force (downward force) against the skin, the underlying tissue, and the artery wall, so as to stop or aid in stopping the flow of blood from the arteriotomy while minimizing the likelihood of collapsing the arterial lumen, which could create thrombosis and occlusion of the artery.

The stationary protruding counter force member or anvil may be implemented in one of multiple configurations. The counter force member can be a single flat surface, a rib configured as a longitudinal keel, a cross-pattern, a cylindrical boss, or a series of concentric bearing surfaces, for example. The distal margin of the counter force member which contacts the skin and compresses the tissues can be shaped to be flat or convex, for example.

In some embodiments, the arteriotomy closure device may include a housing. The housing may further include an open volume, which may be at least partially open, and may further include a bottom surface to the housing. The device may include a means for applying a force, though this means may take the form of multiple means of force generation or force utilization, such as a mechanical feature or a suctional feature, among others. The device may further include a securement band. The band may have a top surface and may have a bottom surface. The device may also include an anvil feature or component, which may be integral or separate from other components of the device. The anvil may optionally be disposed at least partially within the open volume within the housing and may also optionally include a surface, such as a bottom surface.

The securement band may include a securement feature to aid in retention of the securement band, or at least a portion of the securement band, to a patient's skin, such as retaining some or all of the bottom surface of the band to a patient's skin.

The force application feature may be configured such that force is applied to the top surface of the band, or a portion of it, at least within a portion of the housing or where the housing overlays some of the band. The bottom of the housing may be at least partially in contact with a portion of the top of the securement band.

In some embodiments, the force application feature may be a suctional force, such as one created by a fluid displacement member which may create a negative gauge pressure within the open volume of the housing. The feature may be integral with the device, or may be at least partially created separate from the device, wherein fluid displacement is at least partially routed through the device.

The housing may create an airtight seal against at least a portion of the band, such as a footprint of the top of the band, maintaining fluid integrity if desired. The housing may also optionally include one or more windows to enable visualization of a skin puncture site, or may be at least partially transparent or translucent.

The device, or one or more portions of the device, may define a channel to receive or aid or enable the usage of an introducer sheath while maintaining a negative gauge pressure within the open volume of the housing.

The anvil of the device may include a bottom surface which may be substantially planar, may be curved, such as being convex or concave, may have one or more protrusions, or may have one or more recesses. The bottom of the anvil may be substantially planar with the bottom of the housing, may be below the bottom of the housing, such as being relatively distal to a user, or may be above the bottom of the housing, such as being at least partially recessed within the housing and being relatively proximal to a user.

The device may be transitioned from an undeployed configuration to a deployed configuration, such as when the force generation feature is active. When in a deployed configuration, such as when suction is applied, the anvil bottom surface may apply force to a patient's skin, subcutaneous tissue, and artery. The device may include a suction retention feature to retain suction, or otherwise retain tissue against the anvil, when in a deployed configuration. In some embodiments, a syringe or syringe plunger may be used to create negative gauge pressure within the housing, though other means may also be used without deviating from the scope or intent of this disclosure.

The anvil of the device may be directly or indirectly connected to an inner wall of the housing, or may be connected above the suction chamber or open volume. The anvil may be integral with other components of the device or may be a separate component.

The bottom of the housing may be integral or separate from the securement band. In some embodiments, the housing is made of a rigid or substantially rigid material while the band may be made of a flexible material. The housing may optionally be secured to the band, such as by means of an adhesive or chemical weld, or may be retained by other means, such as mechanical means. The band itself may be retained, or partially retained, against a patient's skin through various means, such as through the use of an adhesive, which may be removable.

The method may include the use of an arteriotomy closure device, system, or kit which may include one or more of the features or components described herein. Any number of components or features may be used in conjunction with and incorporated into the device described. Various materials, including metals, plastics, and composites, may be used for the described components and features.

It is to be understood that the above mentioned features and the features yet to be explained hereinafter can be used not only in the respectively mentioned combinations but also in other combinations or alone without departing from the context of the present invention.

BRIEF DESCRIPTION OF THE DRAWINGS

The invention is now disclosed in detail with reference to exemplary embodiments shown in the accompanying drawings, where.

DETAILED DESCRIPTION

Figure 1:
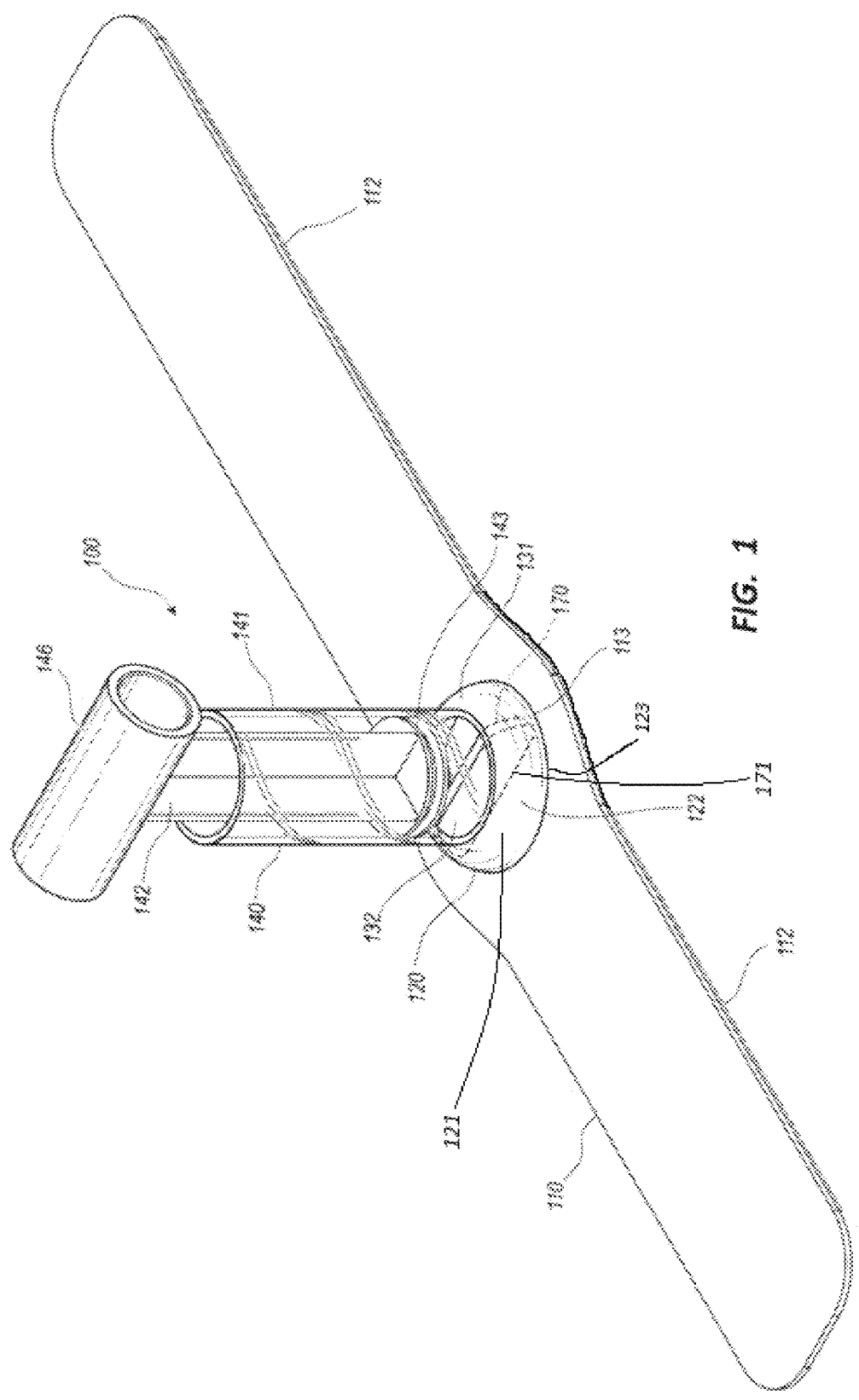
FIG. 1 shows a top perspective view of an embodiment of an arteriotomy closure device of the present disclosure.

Exemplary embodiments of the disclosure are illustrated in the Figures and are explained in the following description in more detail, wherein identical reference numbers refer to identical, or similar, or functionally identical or similar components.

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features or those previously described are omitted or simplified in order not to obscure the illustrative embodiments.

Various operations may be described as multiple discrete operations, in turn, in a manner that is most helpful in understanding the present invention, however the order of description should not be construed as to imply that these operations are necessarily order dependent. In particular, these operations need not be performed in the order of presentation. In some instances, structures and devices may be shown in block diagram or flow chart form in order to facilitate describing the disclosed subject matter.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the housing of an arteriotomy closure device, the proximal end of the housing refers to the top of the housing which is away from the patient's skin and the distal end refers to the opposite end, the end nearest the patient's skin when the arteriotomy closure device is in use. Thus, if at one or more points in a procedure a physician changes the orientation of the housing, as used herein, the term "proximal end" always refers to the top end of the housing (even if the distal end is temporarily closer to the physician).

"Fluid" is used in its broadest sense, to refer to any fluid, including both liquids and gases as well as solutions, compounds, suspensions, etc., which generally behave as fluids.

FIGS. 1-14 illustrate different views of several arteriotomy closure devices and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 shows an embodiment of an arteriotomy closure device 100 wherein positive displacement, or upward displacement of the skin, subcutaneous tissue, and artery are facilitated by means of the application of suction, or vacuum, applied to the proximal surface of a securement band which may be adhesively bonded to the skin of a patient overlying an arteriotomy. The arteriotomy closure device 100 includes a housing 120, a counter force member or anvil 170, a fluid displacement or suction member 140, and a securement band 110. The housing 120 may have a generally round shape and may be formed from a material that is sufficiently sufficiently rigid to withstand negative gauge pressure applied within the housing and not collapse, though other shapes, including compound shapes, may also be used without deviating from the scope or intent of the disclosure. For example, in the embodiment, the housing 120 may be formed from a rigid or semi-rigid material, such as polycarbonate, high density polyurethane, polypropylene, etc. The housing 120 can be formed using any suitable manufacturing technique, such as injection molding, casting, 3-D printing, or other means known in the art. The housing may be transparent or translucent to allow a user to view the inside of the housing 120.

The housing 120, as illustrated in the depicted embodiment of FIG. 1, includes a side wall 122 extending distally from a top surface 131. The side wall 122 terminates at a distal sealing surface 123. The housing 120 and/or the distal sealing surface 123 may consist of flat features to effectively hold negative gauge pressure when adhesively bonded to the proximal surface 110 of the securement band 111. The distal sealing surface 123 may include a smooth, flat surface with a width that is equivalent to a thickness of the side wall 122. The side wall 122 and the top surface 131 of the housing 120 can define a suction chamber 121. The distal sealing surface 123 may be unitary with the housing 120 or may be a separate component or material, such as one which may optionally be bonded to the housing 120.

The anvil 170 is shown in the illustrated embodiment of FIG. 1 disposed within the suction chamber 121 and extending distally from the top surface 131. The anvil 170 may optionally divide the suction chamber 121 into at least two portions, though some embodiments may not divide the suction chamber 121. The anvil 170 includes a distal end 171 which is flush with the distal sealing surface 123. In other embodiments, the distal end 171 may be recessed into the suction chamber 121. The anvil 170 may be integral with the housing 120 and formed from the same material as the housing 120. In other embodiments, the anvil 170 may be a separate component of a different material and coupled to the housing using any suitable technique, such as over molding, gluing, bonding, etc. In certain embodiments, the anvil 170 may be flexible. In other embodiments, the anvil 170 may be rigid or semi-rigid.

The anvil 170 may be of any suitable shape such that when adhesively bonded to the proximal surface 110 of the securement band 110, it provides a stable, stationary platform against which the patient's skin, subcutaneous tissue and artery are drawn proximally against the distal end 171 of the anvil 170 to close an arteriotomy. FIGS. 2A-5B depict exemplary shapes of the anvil 170. Any one of the exemplary anvil shapes may be used with any one of the arteriotomy closure embodiments disclosed herein.

Figures 2A, 2B, 3A, 3B, 4A, 4B, 5A, 5B:
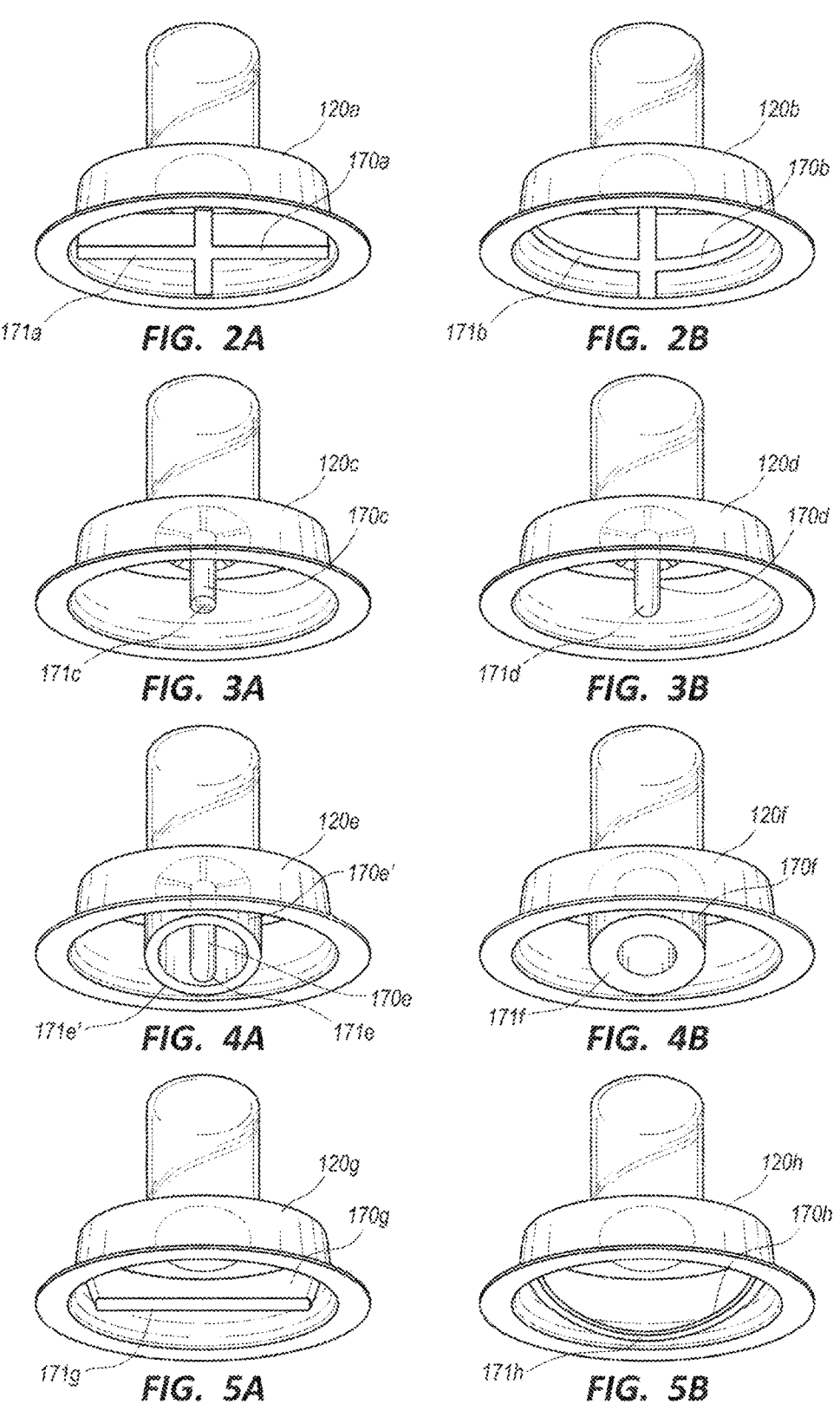
FIG. 2A shows a bottom perspective view of an embodiment of a housing of a suction chamber and an anvil disposed therein of an arteriotomy closure device of the present disclosure.
FIG. 2B shows a bottom perspective view of another embodiment of a housing of a suction chamber and an anvil disposed therein of an arteriotomy closure device of the present disclosure.
FIG. 3A shows a bottom perspective view of an alternate embodiment of a housing of a suction chamber and an anvil disposed therein of an arteriotomy closure device of the present disclosure.
FIG. 3B shows a bottom perspective view of an embodiment of a housing of a suction chamber and an anvil disposed therein of an arteriotomy closure device of the present disclosure.
FIG. 4A shows a bottom perspective view of another embodiment of a housing of a suction chamber and an anvil disposed therein of an arteriotomy closure device of the present disclosure.
FIG. 4B shows a bottom perspective view of an alternate embodiment of a housing of a suction chamber and an anvil disposed therein of an arteriotomy closure device of the present disclosure.
FIG. 5A shows a bottom perspective view of an embodiment of a housing of a suction chamber and an anvil disposed therein of an arteriotomy closure device of the present disclosure.
FIG. 5B shows a bottom perspective view of another embodiment of a housing of a suction chamber and an anvil disposed therein of an arteriotomy closure device of the present disclosure.

Turning to FIG. 2A, a bottom perspective view of a housing 120a is shown. FIG. 2A illustrates an anvil 170a configured as a cross pattern. Turning to FIG. 2B, a bottom perspective view of a housing 120b is shown. FIG. 2B illustrates an anvil 170b configured as a cross pattern with a substantially curved, or convex, distal end 171b. Turning to FIG. 3A, a bottom perspective view of a housing 120c is shown. FIG. 3A illustrates an anvil 170 configured as a central cylindrical boss with a flat distal end 171c.

Turning to FIG. 3B, a bottom perspective view of a housing 120d is shown. FIG. 3B illustrates a central cylindrical anvil 170d with a substantially smooth radiused distal end 171d.

Turning to FIG. 4A, a bottom perspective view of a housing 120e is shown. FIG. 4A illustrates a configuration of a central cylindrical anvil 170e with a substantially smooth radiused distal end 171e. A concentric outer cylindrical anvil 170e' surrounds the central anvil 170e. Both the distal end 171e of the central cylindrical anvil 170e and the distal end 171e' of the concentric outer cylindrical anvil 170e' are configured such that they extend the same distance in the distal direction (i.e., the distal ends 171e, 171e' of both anvils 170e, 170e' are coplanar).

Turning to FIG. 4B, a bottom perspective view of a housing 120f is illustrated. FIG. 4B shows a cylindrical anvil 170f with a substantially flat distal end 171f. A distal end 171f of the anvil 170f may also include a coating of indicia such that the indicia aid the operator in aligning the housing 120f and the anvil 170f to be centered directly over an arteriotomy.

Turning to FIG. 5A, a bottom perspective view of a housing 120g is shown. FIG. 5A illustrates an anvil 170g configured as a central longitudinal rib, or keel. A distal end 171g of the anvil 170g may include a coating of indicia such that the indicia aid the operator in aligning the housing 120g and the anvil 170g to be centered directly over an arteriotomy.

Turning to FIG. 5B, a bottom perspective view of a housing 120h is shown. FIG. 5B illustrates an anvil 170h configured as a central longitudinal rib, or keel having a curved or convex distal end 171h.

Referring again to FIG. 1, the illustrated embodiment of the arteriotomy closure device 100 shows the fluid displacement or suction member 140 extending upwardly from the housing 120. The suction member 140 can include a barrel 141 and a plunger 142. The barrel 141 can be integrally formed with the housing 120 and be formed from the same material as the housing 120. In other embodiments, the barrel 141 can be a separate component and be coupled to the housing 120 using any suitable technique, such as bonding, gluing, welding, friction fit, etc. In this embodiment, the barrel 141 may be formed from the same or different material than the housing 120. The housing 120 may include a port 132 disposed between the suction chamber 121 and the barrel 141 such that the suction chamber 121 is in fluid communication with the barrel 141.

The plunger 142 is disposed within the barrel 141 and is configured to be longitudinally displaced from a distal position to a proximal position. The plunger 142 may include a plunger tip 143 coupled to a distal end of the plunger 142. The plunger tip 143 may be configured to seal against an internal surface of the barrel 141. A plunger grip 146 may be disposed at a proximal end of the plunger 142. The plunger grip 146 may be of any suitable shape that allows a user to easily grip the plunger 142 for longitudinal displacement. For example, as illustrated in FIG. 1, the plunger grip 146 can be in the form of a transversely oriented cylinder. In other embodiments, the plunger grip 146 may be in the form of a transverse flange, a bulb, a ring, etc. In certain embodiments, the plunger 142 may be held in the proximal position via a plunger retention member in order to maintain continuous vacuum in the suction chamber 121. For example, the plunger retention mechanism may be a ratchet mechanism or detent-type holding mechanism or any other suitable mechanism configured to hold the plunger 142 in a longitudinal position.

As shown in FIG. 1, the housing 120 may be coupled to a securement band 110. The securement band 110 may be configured to be disposed around a portion of a patient's limb in order to secure the housing 120 over an arteriotomy site. For example, the securement band 110 may be a wrist band configured to be disposed around a wrist of a patient such that the housing 120 can be secured over a radial, ulnar or palmar artery arteriotomy site. In other embodiments, the securement band 110 may be configured to be disposed around a patient's hand, thigh, ankle, upper arm, etc. In some embodiments the palmar artery may be accessed at the anatomical snuffbox of the patient. The securement band 110 may be formed of a flexible, low modulus/low durometer polymeric membrane and include a "peel and stick" distal surface 112 to be adhesively fixed to the skin when disposed around a portion of the patient's limb.

In use, following an arterial catheterization procedure and prior to removal of an introducer sheath, the arteriotomy closure device 100 may be positioned on a portion of a limb of a patient such that the housing 120 is disposed over an arteriotomy site. In certain embodiments, the housing 120 may be disposed over the arteriotomy site, a skin puncture site, and/or a skin tract between the arteriotomy site and the skin puncture site. The securement band 110 may be wrapped around the portion of the limb with its distal surface 112 positioned to be adhesively connected to the patient's skin. The securement band 110 may be held tightly to the patient's skin such that its distal surface 112 provides a proximally directed pulling force on the patient's skin when air is evacuated from the suction chamber 121. The plunger 142 can be displaced from the distal position to the proximal position to generate a suction within the barrel 141 and the suction chamber 121. The plunger 142 may be locked in the proximal position by the plunger retention member. The suction within the suction chamber 121 may cause the securement band to be drawn, or distended, in a proximal, or puckered, position toward the housing 120 and anvil 170. By way of the adhesive attachment of the securement band to the patient's skin, the skin, subcutaneous tissue and artery are likewise drawn, or distended, in a proximal, or puckered, position toward the housing 120 and anvil 170 such that the anvil 170 applies a counter force against the patient's skin overlying the arteriotomy and/or a tissue tract which facilitates hemostasis, or cessation of bleeding, from the arteriotomy. In certain embodiments, a suction force is formed or induced (i.e., negative gauge pressure is induced) in the suction chamber 121 prior to removal of the introducer sheath from the artery. In other embodiments, the introducer sheath is removed from the artery prior to inducing suction in the suction chamber 121 or simultaneously as negative gauge pressure is induced.

When cessation of bleeding from the skin puncture site has been achieved after a set period of time, the plunger 142 may be moved to the distal position such that the suction in the suction chamber 121 is relieved and atmospheric pressure inside the suction chamber 121 is restored, thus removing the counter force provided by the anvil 170 against the patient's skin. At this time, the arteriotomy closure device 100 may be removed from the patient's limb.

Figure 6:
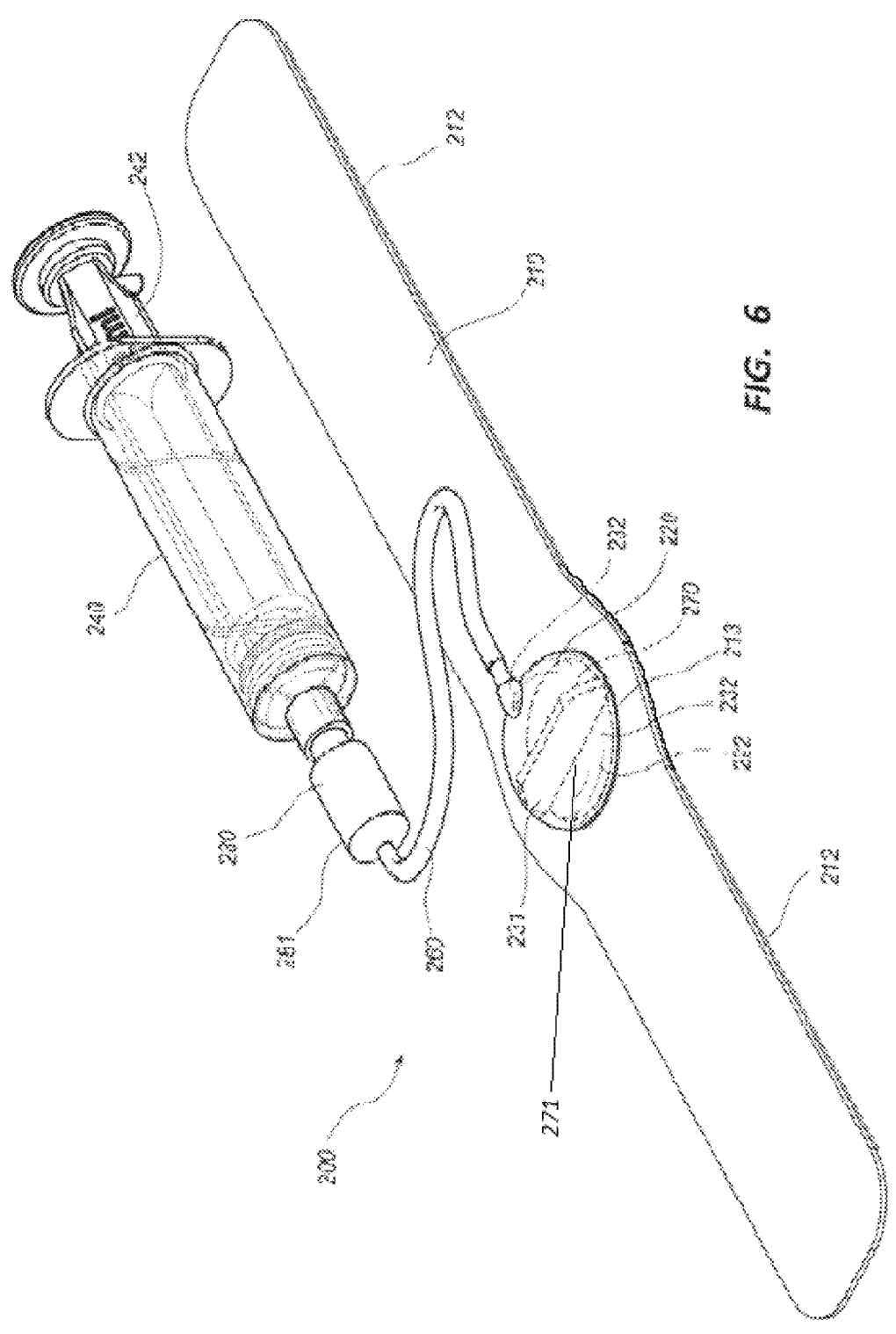
FIG. 6 shows a top perspective view of an embodiment of an arteriotomy closure device of the present disclosure.

FIG. 6 depicts an embodiment of an arteriotomy closure device 200 that resembles the arteriotomy closure device 100 described above in certain respects. Accordingly, like features are designated with like reference numerals, with the leading digit incremented to "2." For example, the embodiment depicted in FIG. 6 includes a housing 220 that may, in some respects, resemble the housing 120 of FIG. 1. Relevant disclosure set forth above regarding similarly identified features thus may not be repeated hereafter. Moreover, specific features of the arteriotomy closure device 100 and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the arteriotomy closure device 200 and related components depicted in FIG. 6. Any suitable combination of the features, and variations of the same, described with respect to the arteriotomy closure device 100 and related components illustrated in FIG. 1, can be employed with the arteriotomy closure device 200 and related components of FIG. 6, and vice versa. This pattern of disclosure applies equally to further embodiments depicted in subsequent figures and described hereafter, wherein the leading digits may be further incremented FIG. 6 illustrates an embodiment of an arteriotomy closure device 200. The arteriotomy closure device 200 includes a housing 220, a counter force member or anvil 270, an extension tubing 260, a valve member 280, and a securement band 210. The housing 220 may have a generally elliptical shape and may be formed from any suitable material. For example, in one embodiment, the housing 220 may be formed from a rigid or semi-rigid material, such as polycarbonate, high density polyurethane, polypropylene, etc., such that the housing is formed with a contour shape configured to conform to the anterior aspect of the patient's wrist. The housing 220 can be formed using any suitable manufacturing technique, such as injection molding, casting, 3-D printing, etc. The housing may be transparent or translucent to allow a user to view the inside of the housing 220.

The housing 220, as illustrated in the depicted embodiment of FIGS. 6, includes a side wall 222 extending distally from a top surface 231. The side wall 222 terminates at a distal sealing surface 213. The distal sealing surface 223 may include a flange 224 extending radially outward from the distal sealing surface 223. The flange 224 may be configured to increase a surface area of the sealing surface 223 to enhance sealing of the housing 220 against the proximal surface of the securement band. In other embodiments, the distal sealing surface 223 may include a smooth, flat surface with a width that is approximately equivalent to a thickness of the side wall 222. The side wall 222 and the top surface 231 of the housing 220 can define a suction chamber 221 along with the top surface of the securement band.

The counter force member or anvil 270 is shown in the illustrated embodiment of FIG. 6 to be disposed within the suction chamber 221 and to extend distally from the top surface 231. The anvil 270 can divide the suction chamber 221 into at least two portions. The anvil 270 includes a distal end 271 which may be recessed into the suction chamber 221. In other embodiments, the distal end 271 may be flush with the sealing surface 223. The anvil 270 may be integral with the housing 220 and formed from the same material as the housing 220. In other embodiments, the anvil 270 may be a separate component of a different material and coupled to the housing using any suitable technique, such as over molding, gluing, bonding, etc. In certain embodiments, the anvil 270 may be flexible. In other embodiments, the anvil 270 may be rigid or semi-rigid.

The anvil 270 may be of any suitable shape such that a patient's skin, subcutaneous tissue, and artery can be drawn against the distal end 271 of the anvil 270 to close an arteriotomy. FIGS. 2A-5B depict exemplary shapes of the anvil 270. Any one of the exemplary anvil shapes may be used with the arteriotomy closure device 200.

The housing 220, in the illustrated embodiment of FIG. 6 includes a port 232 extending radially outwardly from the housing 220. The port 232 is in fluid communication with the suction chamber 221. A distal end of an extension tube 260 is coupled to the port 232. A suction retention member may be coupled to the extension tube. In one embodiment the suction retention member comprises a valve member 280 coupled to the extension tube 260. The valve member 280 may be configured to retain a suction force or negative gauge pressure within the suction chamber 221. In the illustrated embodiment of FIG. 6, the valve member 280 is a check-valve 281. The check-valve 281 is coupled to a proximal end of the extension tube 260 such that the check-valve is in fluid communication with the suction chamber 221. The check-valve 281 may be selectively opened to allow a negative gauge pressure or suction force to be induced or formed in the suction chamber 221 and selectively closed to retain the negative gauge pressure or suction force in the suction chamber 221. In other embodiments, the valve member 280 may be of any suitable type capable of selectively opening and closing. For example, the valve member may be a pinch clamp, a slide clamp, a pinch valve, etc.

As shown in FIG. 6, the housing 220 is adhesively bonded to the proximal surface of the securement band 210. The securement band 210 may be configured to be disposed around a portion of a patient's limb such that its distal surface includes a "peel and stick" adhesive coating 212 in order to secure the securement band 210 as coupled to the housing 220, over an arteriotomy site. For example, the securement band 210 may be a wrist band configured to be disposed around a wrist of a patient such that the housing 220 can be positioned over a radial or ulnar artery arteriotomy site. In other embodiments, the securement band 210 may be configured to be disposed around a patient's hand, thigh, ankle, upper arm, etc. The securement band 210 may be formed of a flexible, low modulus/low durometer, air impermeable polymeric membrane that includes a distal "peel and stick" surface 212 that provides an adhesive bond with the skin sufficient to provide the necessary proximally directed pulling force to draw the skin, subcutaneous tissue and artery in a proximal direction when suction, or negative pressure, is induced in the housing 220.

In use, following an arterial catheterization procedure and prior to removal of an introducer sheath, the arteriotomy closure device 200 may be positioned on a portion of a limb of a patient such that the housing 220 is disposed over an arteriotomy site. In certain embodiments, the housing 220 may be disposed over the arteriotomy site, a skin puncture site, and/or a skin tract between the arteriotomy site and the skin puncture site. The securement band 210 may be wrapped around the portion of the limb and held tightly to the patient's skin. A fluid displacement or suction generating member 240 (e.g., syringe) may be coupled to the check-valve 281. A plunger 242 of the syringe 240 can be displaced from the distal position to the proximal position to generate a suction force or negative gauge pressure within the syringe 240 and the suction chamber 221. The plunger 242 may be locked in the proximal position by a plunger retention member. The suction force within the suction chamber 121 may cause the securement band 210, and concomitantly, the patient's skin, subcutaneous tissue, and artery to be drawn, or distended, in a proximal, or puckered, position toward the housing 220 and anvil 270, such that the anvil 270 applies a counter force against the patient's skin overlying the arteriotomy and/or the tissue tract which facilitates hemostasis, or cessation of bleeding, from the arteriotomy. In certain embodiments, the suction force is formed in the suction chamber 221 prior to removal of the introducer sheath from the artery. In other embodiments, the introducer sheath is removed from the artery prior to the forming of suction force in the suction chamber 221.

When cessation of bleeding from the skin puncture site has been achieved, the plunger 242 may be moved to the distal position such that the suction force in the suction chamber 221 is relieved and atmospheric pressure inside the suction chamber 221 is restored, thus removing the counter force provided by the anvil 270 against the patient's skin. At this time, the arteriotomy closure device 200 may be removed from the patient.

FIGS. 7A-7E illustrate an embodiment of an arteriotomy closure device 300. The arteriotomy closure device 300 includes a housing 320 with a flange 324, a counter force member or anvil 370, a valve member 380, and a securement band 310. The housing 320 may be elliptical or have a circular shape. For example, in one embodiment, the housing 320 may be formed from a rigid or semi-rigid material, such as polycarbonate, high density polyurethane, polypropylene, etc. The housing 320 can be formed using any suitable manufacturing technique, such as injection molding, casting, 3-D printing, etc. The housing may be transparent or translucent to allow a user to view the inside of the housing 320.

The housing 320, as illustrated in the depicted embodiment of FIGS. 7A-7E, includes a side wall 322 extending distally from a top surface 331. The side wall 322 terminates at a distal sealing surface 323. The distal sealing surface 323 may include a smooth, flat surface with a width that is approximately equivalent to a thickness of the side wall 322. In the present embodiment, the housing 320 is sized to include flange 324.

The flange 324 may extend radially outward from the distal sealing surface 323 or side wall 322. The flange 324 may be configured to increase a surface area of the sealing surface 323 to enhance sealing of the housing 320 against the securement band 310.

The flange 324 may include a window, or notch, 328 to facilitate proper placement of the arteriotomy closure device 300 over the arteriotomy both visually (unobstructed view) and physically, by locating the implanted elongate medical device (e.g., an introducer sheath, not shown) between the wings of the flange 324 that form the window, or notch, 328. Consequently, when placed in the window 328, the introducer sheath (not shown) does not disrupt suction or negative gauge pressure. In some embodiments the skin puncture site is disposed below the window, or notch, 328 but outside of the suction chamber 321. In other embodiments, the skin puncture site is disposed within the outside margins of the suction chamber 321.

Furthermore, the anvil 370 may be axially aligned with the window 328 so that placing the introducer sheath (not shown) in the window 328 positions the anvil 370 over the arteriotomy.

The flange 324 may be constructed of the same material as the housing 320 or a material with a similar durometer hardness as the housing 320. In other embodiments, the flange 324 may be more rigid than the housing 320. In yet other embodiments, the flange 324 may be less rigid than the housing 320.

Figure 7A:
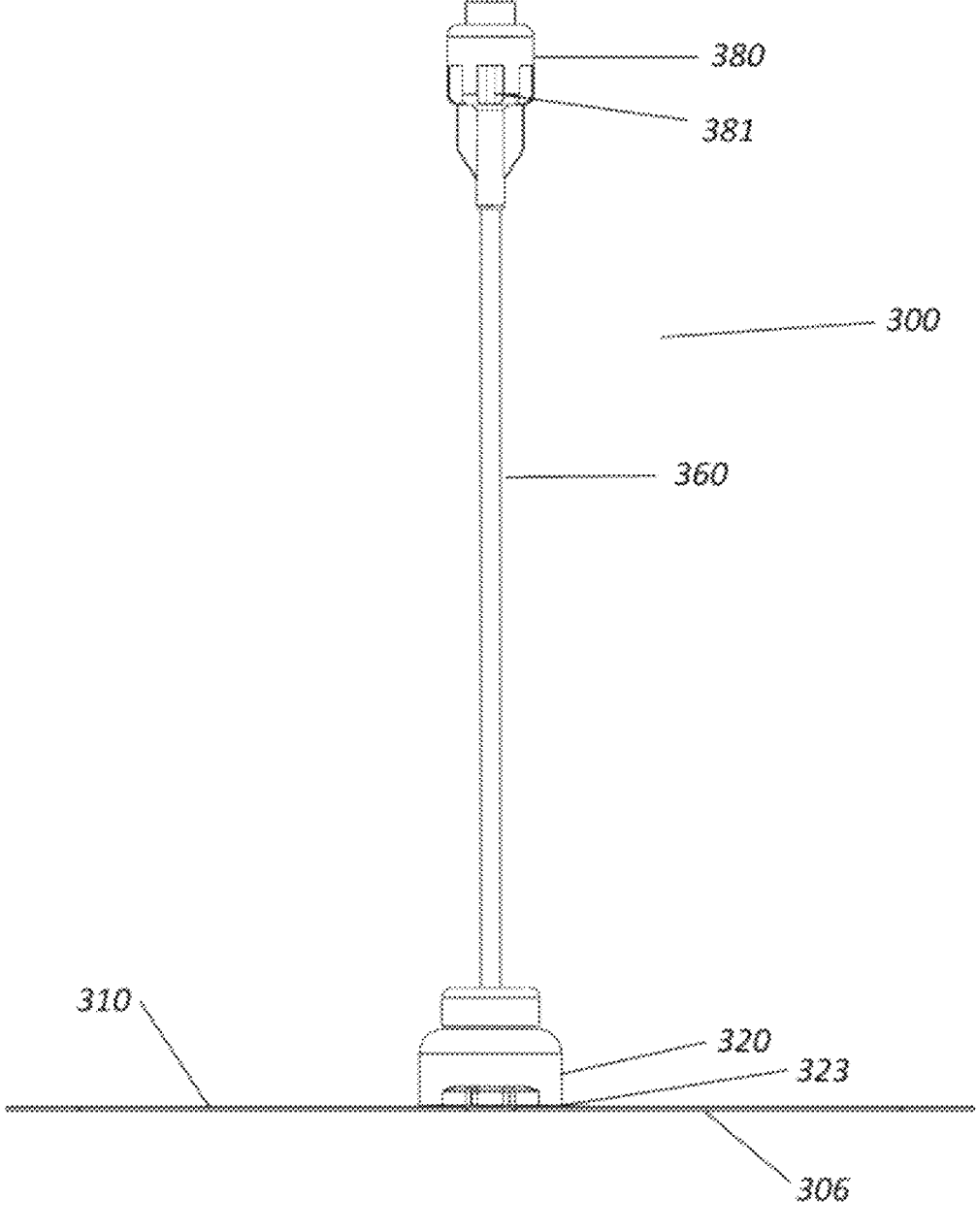
FIG. 7A shows a side view of another embodiment of the arteriotomy closure device of the present disclosure.
Figure 7B:
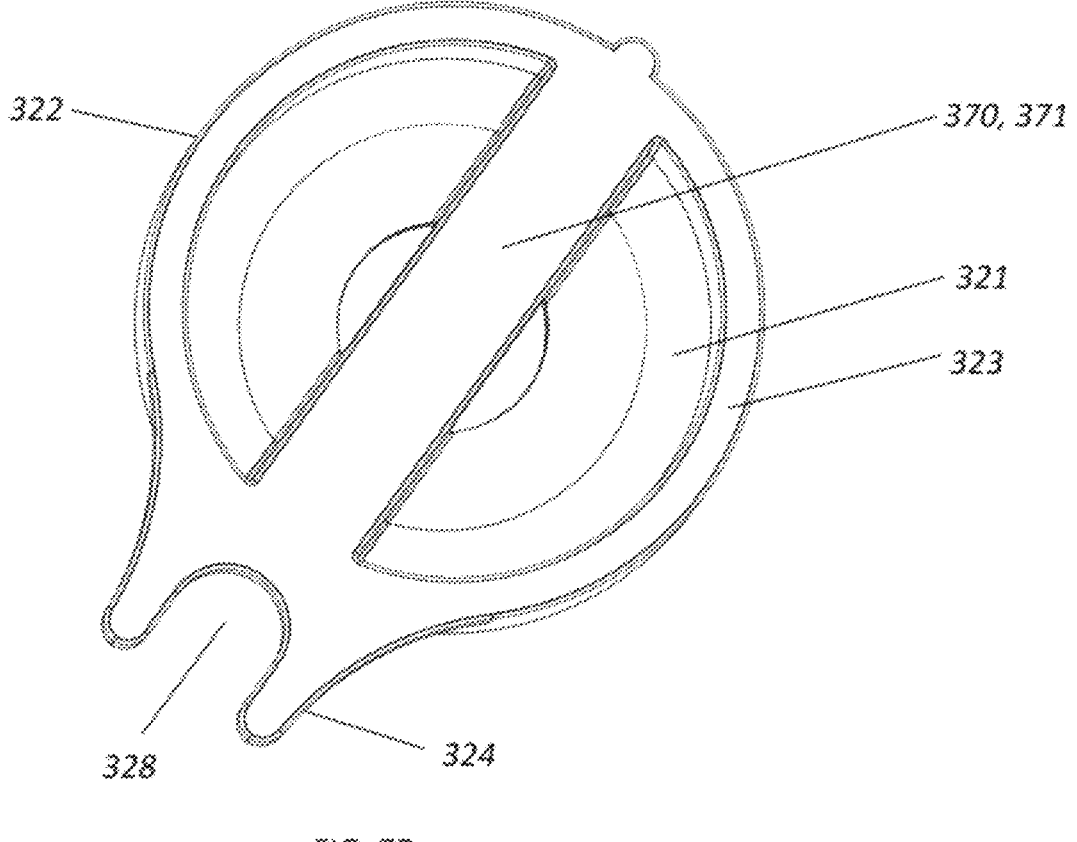
FIG. 7B shows a bottom perspective view of the suction chamber of the embodiment of the arteriotomy closure device of FIG. 7A.

The counter force member or anvil 370 is shown in the illustrated embodiment of FIG. 7B to be disposed within the suction chamber 321 and to extend distally from the top surface 331 (not shown). The anvil 370 can divide the suction chamber 321 into at least two portions. A flow channel (not shown) may be disposed through the anvil 370 such that a suction force or negative gauge pressure can be formed in both portions of the suction chamber 321. The anvil 370 includes a distal end 371 which may be recessed into the suction chamber 321 compared to the distal sealing surface 323. In other embodiments, the distal end 371 of the anvil 370 may be flush with the distal sealing surface 323. The anvil 370 may be integral with the housing 320 and formed from the same material as the housing 320. In other embodiments, the anvil 370 may be a separate component of a different material and coupled to the housing using any suitable technique, such as over molding, gluing, bonding, etc. In certain embodiments, the anvil 370 may be flexible. In other embodiments, the anvil 370 may be rigid or semi-rigid.

The anvil 370 of the embodiment illustrated in FIG. 7B extends across a longitudinal axis of the housing 320. In one embodiment, the anvil 370 length is similar to that of the housing 320, and can be between 0.5 inches and 1.0 inches. In other embodiments the anvil 370 length (and the housing 320 diameter) is between 0.5 inches and 0.75 inches. The distal end 371 of the anvil 370 may be flat and smooth. In other embodiments, the anvil 370 may be of any suitable shape to provide the necessary counterforce against the securement band 310 to close an arteriotomy. FIGS. 2A-5B depict alternative exemplary shapes of the anvil 370. Any one of the alternative exemplary anvil shapes may be used with the arteriotomy closure device 300.

The housing 320, in the illustrated embodiment of FIGS. 7A-7E includes a port 332 disposed through the top surface 331 of the housing 320 to enhance visibility of the internal portion of the housing 320, i.e. the suction chamber 321. The port 332 is in fluid communication with both portions of the suction chamber 321. An extension tube 360 may be coupled to the port 332 at one end. A valve member 380 may be coupled to the extension tube 360 at an opposite end such that the valve member 380 is in fluid communication with the suction chamber 321 through the extension tube 360. The position of the valve member 380 at the end of the extension tube 360 allows the valve member to be accessed by a syringe or other medical device without loss of suction in the suction chamber 321. The valve member 380 may be configured to retain a negative gauge pressure or suction force within the suction chamber 321. In the illustrated embodiment of FIGS. 7A-7E, the valve member 380 is a check-valve 381. The check-valve 381 may be selectively opened to allow a negative gauge pressure or suction force to be formed in the suction chamber 321 and selectively closed to retain the suction force in the suction chamber 321.

Figure 7C:
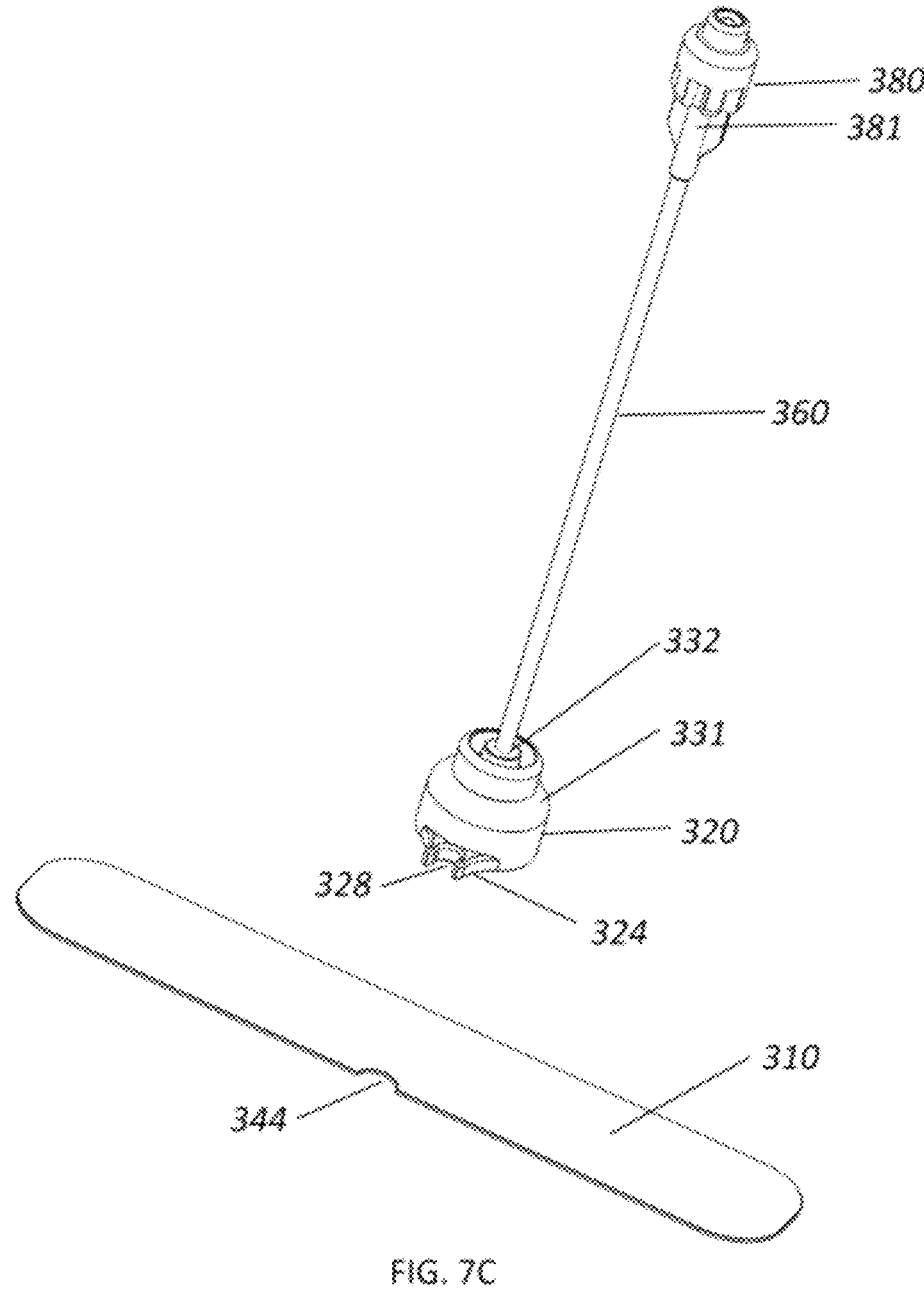
FIG. 7C shows a partially exploded top perspective view of the embodiment of the arteriotomy closure device of FIG. 7A in a not fully assembled configuration.
Figure 7D:
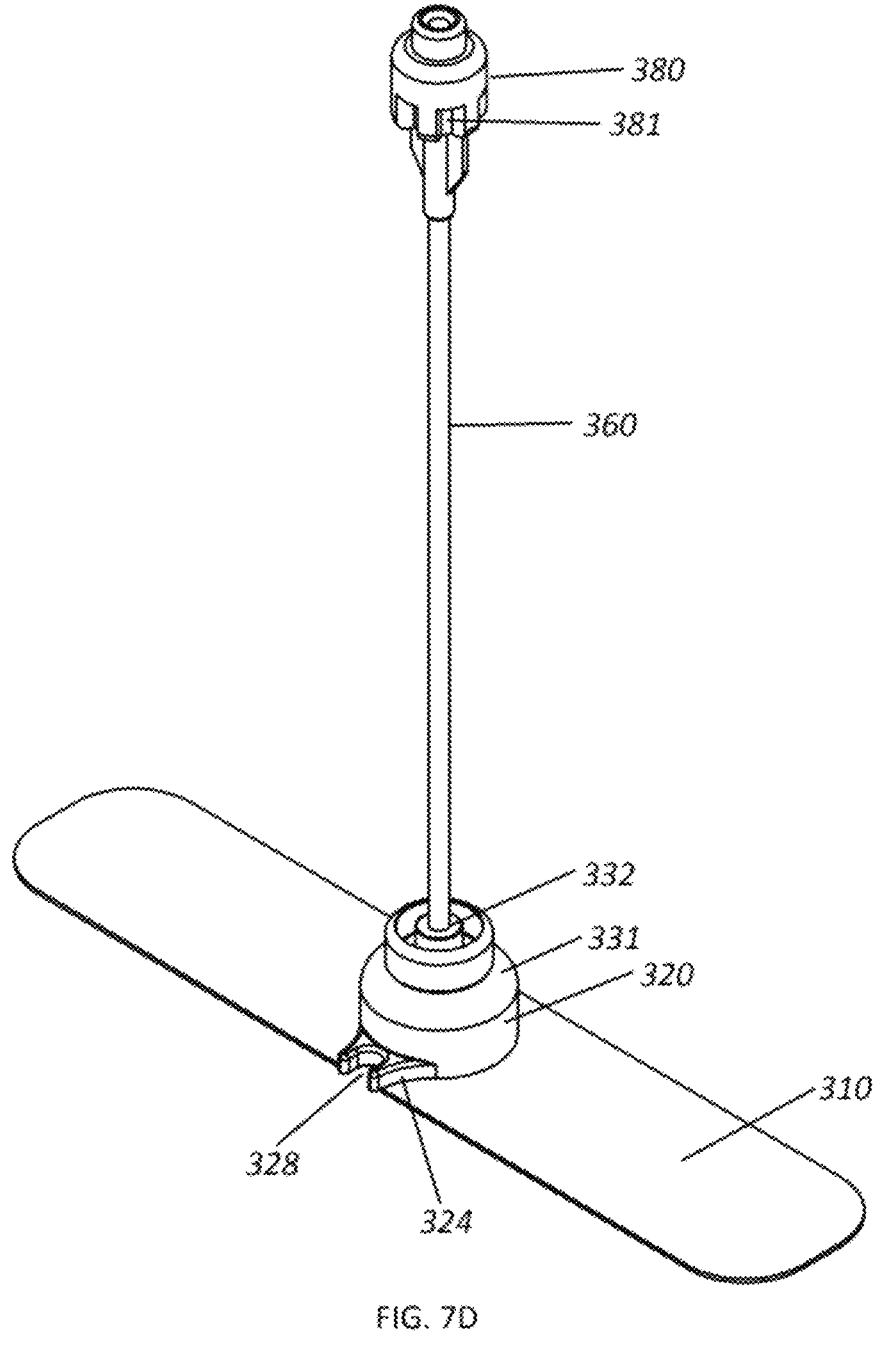
FIG. 7D shows a top perspective view of the embodiment of the arteriotomy closure device of FIG. 7A.

As shown in FIGS. 7B-7D, the housing 320 may be adhesively coupled to the proximal surface of a securement band 310 via adhesive applied to the underside of the housing. The housing 320 may be attached, such as by pressing, through creating contact, or through the application of force, to the top surface of the securement band. In the embodiment shown, the housing is attached to the securement band such that the window, or notch 328, of the flange 324 of the housing 320 aligns with a complimentary notch 344 on the securement band 310. The resulting connection between the housing 320 and the securement band 310 may be substantially air-tight, substantially fluid-tight, and substantially leak-proof.

The securement band 310 may be configured to be disposed around a portion of a patient's limb in order to secure the housing 320 over an arteriotomy site. For example, the securement band 310 may be a wrist band configured to be disposed around the wrist of a patient such that the housing 320 can be secured over a radial or ulnar artery arteriotomy site. In other embodiments, the securement band 310 may be configured to be disposed around a patient's hand, thigh, ankle, upper arm, etc. The securement band 310 may be formed of a low modulus/low durometer polymeric membrane and may include a "peel and stick" distal surface for adhesive fixation to a patient's skin. The adhesive securement band may optionally be foam tape, and may optionally include adhesive or be configured to receive adhesive or otherwise be used with adhesive, and a release liner 306. The adhesive securement band 310 may be constructed from a tape, such as a foam tape (e.g. Polyvinyl Chloride closed-cell foam) and may have an adhesive layer (e.g. an Acrylate adhesive designed for medical/surgical applications) applied to one side of the PVC foam or other band material. The adhesive band may optionally include a release liner (e.g. a super-calendered Kraft paper with silicone on the adhesive contacting surface).

In one method of use, the device may be assembled by adding adhesive (e.g. cyanoacrylate, UV cure adhesive, etc.) so as to bond components together and to create connections which are substantially air-tight or fluid-tight and may be leak-proof.

Figure 7E:
FIG. 7E shows a top perspective view of a portion of the arteriotomy closure device of FIG. 7A in an environment where it has been applied to the limb of a patient.

In use, as depicted in FIG. 7E, following an arterial catheterization procedure and prior to removal of an introducer sheath (not shown), the arteriotomy closure device 300 may be positioned on a portion of a limb of a patient such that the housing 320 is disposed over an arteriotomy site by locating the introducer sheath (not shown) within the window 328 of the flange 324, whereby the securement band 310 may be wrapped around a portion of the limb of a patient. In other embodiments, the housing 320 may be disposed directly over the arteriotomy site, a skin puncture site, and/or a skin tract between the arteriotomy site and the skin puncture site.

A syringe may be coupled to the check-valve 381. A plunger of the syringe can be displaced from a distal position to a proximal position to generate a negative gauge pressure or suction force within the syringe and the suction chamber 321. The plunger may be locked in the proximal position by an optional plunger retention member. The suction force within the suction chamber 321 and subsequent pulling of the securement band in a proximal direction may cause the patient's skin, subcutaneous tissue, and artery to be drawn, or distended, in a proximal, or puckered, position toward the housing 320 and anvil 370, such that the anvil 370 applies a counter force against the patient's skin overlying the arteriotomy and/or the tissue tract which facilitates hemostasis, or cessation of bleeding, from the arteriotomy via concomitant downward reactive counterforce. The equal and opposite forces act to compress the skin and subcutaneous tissue overlying the artery, which may effect hemostasis without compression of the arterial lumen. In certain embodiments, the suction force is formed in the suction chamber 321 prior to removal of the introducer sheath from the artery. In other embodiments, the introducer sheath is removed from the artery prior to forming of the suction force in the suction chamber 321.

When cessation of bleeding from the skin puncture site has been achieved, the plunger may be moved to the distal position such that the suction force in the suction chamber 321 is relieved and atmospheric pressure inside the suction chamber 321 is restored, thus removing the counter force provided by the anvil 370 against the patient's skin. At this time, the arteriotomy closure device 300 may be removed from the patient's limb by peeling the adhesive connection of the securement band in the same manner in which a band-aid is removed from skin.

Figure 8A:
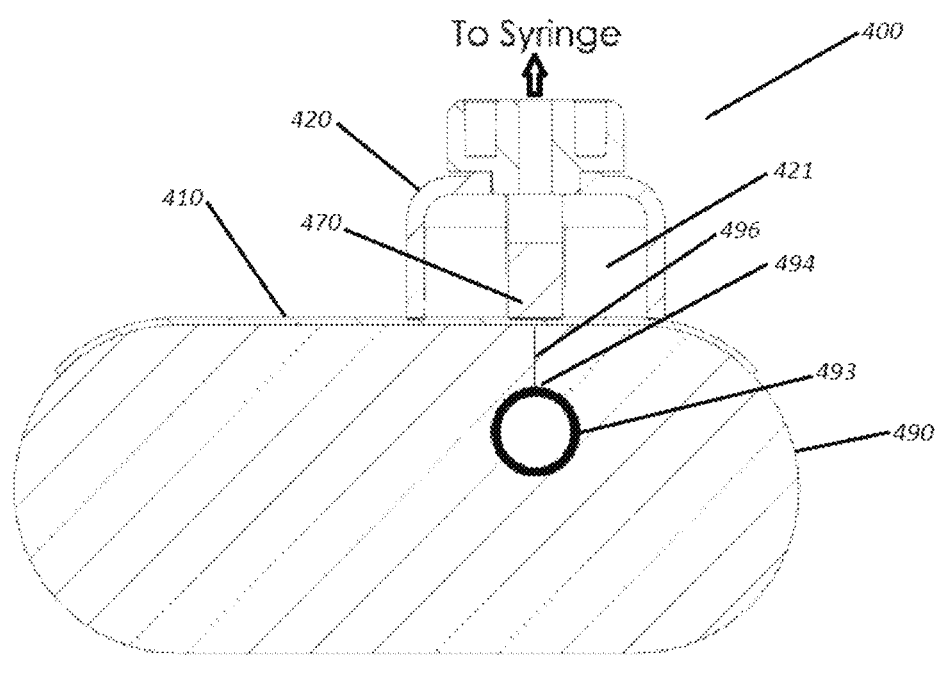
FIG. 8A shows a cross-sectional view of an arteriotomy closure device of the present disclosure in an environment where it is coupled to a limb of a patient without suction.

FIG. 8A illustrates a transverse cross-sectional view of an arteriotomy closure device 400, similar to the arteriotomy closure device 300 previously described, coupled to a wrist 490 of a patient in a pre-suction state. The arteriotomy closure device 400 includes a housing 420, a suction chamber 421 and a counterforce member or anvil 470 and a securement band 410. The housing 420 is adhesively attached to the securement band 410 and the securement band 410 is adhesively attached to the patient's skin and positioned over a blood vessel 493 (e.g., artery). The counterforce member 470 is positioned in axial alignment over the blood vessel 493. The blood vessel 493 includes an arteriotomy 494 through a wall of the blood vessel. A tissue tract 496 extends between the arteriotomy 494 and a skin puncture site at the skin surface 490 such that the arteriotomy 494 is in fluid communication with the skin puncture surface 491. The housing 420 and the securement band 410 may be positioned on the wrist 490 such that the skin puncture site is disposed exterior to the suction chamber 421. In other embodiments, the skin puncture site may be disposed under the suction chamber 421 and beneath the anvil 470.

Figure 8B:
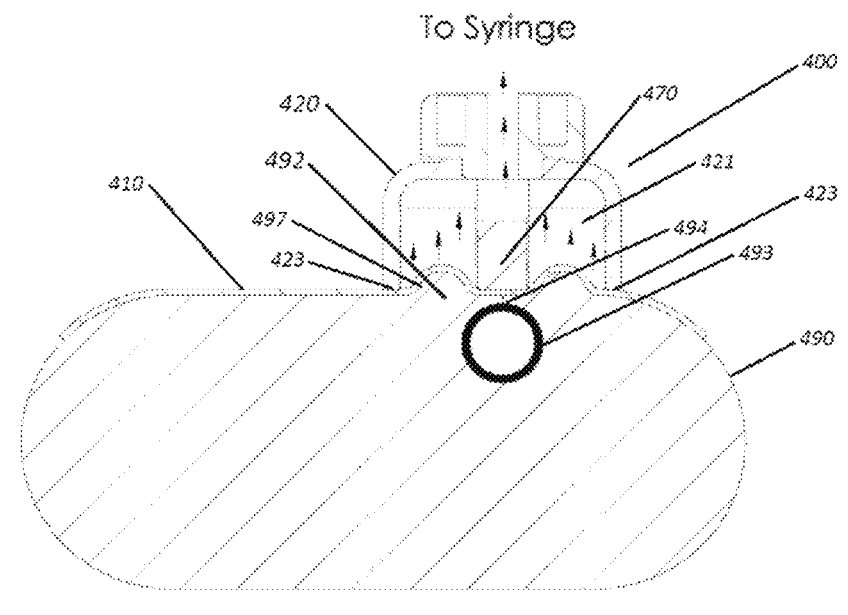
FIG. 8B shows a cross-sectional view of the arteriotomy closure device of FIG. 14A in an environment where it is coupled to a patient's limb with suction.

FIG. 8B illustrates a transverse cross-sectional view of the arteriotomy closure device 400 coupled to the wrist 490 in a suction state. The suction chamber 421 contains a negative gauge pressure or suction force. The amount of fluid displaced to achieve a desired negative gauge pressure may be, in some embodiments, between 5-30 mL. In other embodiments, the amount of fluid displaced to achieve a desired negative gauge pressure is between 5-10 mL, though other displacements may also be created without deviating from the scope or intent of this disclosure. The distal sealing surface 423 forms an airtight seal to the proximal surface of the securement band 410 and the securement band 410 is adhesively attached to the skin surface 497 of the wrist 490. The skin surface 497 of the wrist 490, along with the securement band 410 within the perimeter of the distal sealing surface 423 is drawn or puckered into the suction chamber 421 causing subcutaneous tissue 492 and the blood vessel 493 to be drawn upward. The proximal surface of the securement band 410 is drawn against the counterforce member 420 causing the subcutaneous tissue 492 to be compressed, i.e. as the securement band 410 rises away from the core of the patient's limb, the skin surface 490 and the arterial lumen 493 may be pulled upward while the counterforce member, or central keel, or anvil, 470 inside the suction chamber 421 concomitantly applies a downward reactive counterforce. Compression of the subcutaneous tissue 492 causes closure of the tissue tract 496 and the arteriotomy 494 while not applying a distorting displacement to the blood vessel 493. Closure of the tissue tract 496 and the arteriotomy 494 may result in cessation of blood flow from the skin surface 490. In some embodiments, it may take between 15 minutes and 6 hours of the application of negative gauge pressure to achieve and maintain hemostasis. In other embodiments, it may take between 2 and 3 hours of the application of negative gauge pressure to the treatment site to achieve and maintain hemostasis.

Figure 9A:
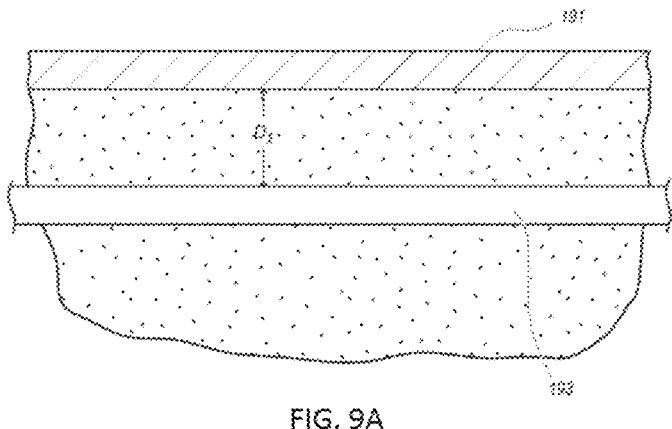
FIG. 9A shows a schematic illustration of a longitudinal ultrasound image of a portion of an exemplary patient's limb without a suction force applied to a skin surface.

FIG. 9A is an illustration of a sonogram image produced from an ultrasound examination of a patient's right radial artery 193 in a lateral, longitudinal orientation. The artery 193 is shown in a natural state whereby the arterial lumen 197 is fully perfused with blood, prior to a proximally directed, or upward, force being applied to the skin surface 191 by any arteriotomy closure devices disclosed herein. It can be seen from the illustration of FIG. 15A that the longitudinal orientation of the artery 193 is substantially parallel with the patient's skin surface 191. The artery 193 is also shown at a depth of $D_1$ below the skin surface 191.

Figure 9B:
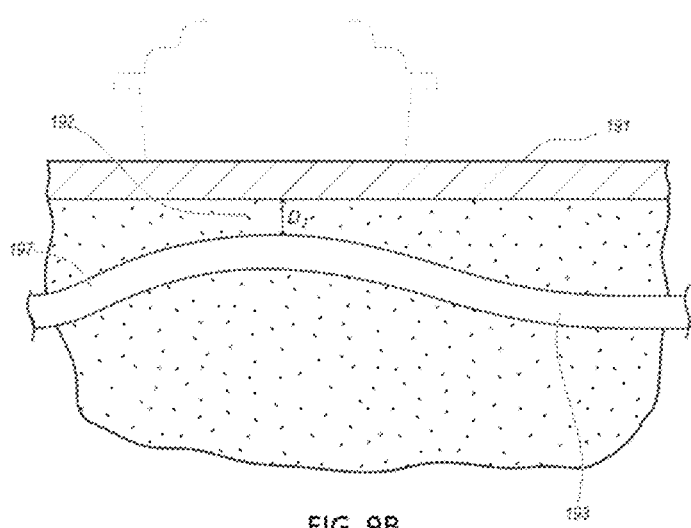
FIG. 9B shows a schematic illustration of a longitudinal ultrasound image of a portion of an exemplary patient's limb with a suction force applied to a skin surface.

FIG. 9B is an illustration of a sonogram image produced from an ultrasound examination of the right radial artery 193 in a lateral, longitudinal orientation. The artery 193 is shown in a state where a proximally directed, or upward, force is applied to the skin surface 191 directly overlying the artery 193. It can be seen from the illustration of FIG. 9B that the longitudinal orientation of the artery 193 has been substantially altered by the application of the upward force such that the artery 193 is bowed in an upward direction, i.e., the upward pulling force applied to the skin surface 191 has reoriented the artery 193 from being substantially parallel with the skin surface 191 to being bow-shaped. It can further be seen that the depth $D_2$ of the artery 193 is less than the depth $D_1$ (in FIG. 9A) due to compression of subcutaneous tissue 192. It can additionally be seen from the illustration that the arterial lumen 197 remains fully perfused with blood during the application of suction to the skin surface 191 directly overlying the artery 193.

Figures 10A, 10B:
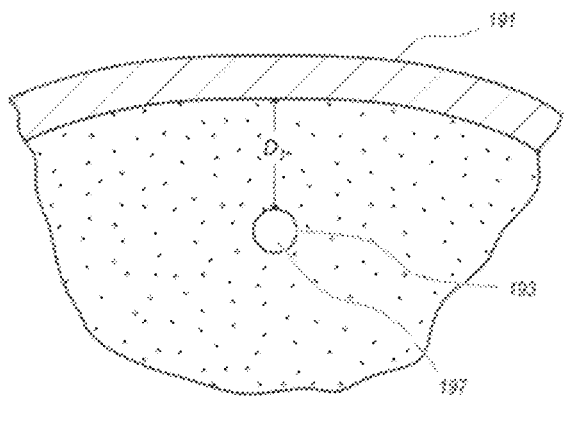
FIG. 10A shows a schematic illustration of a transverse cross-sectional view of a portion of an exemplary patient's limb without a suction force applied to a skin surface.
FIG. 10B shows a schematic illustration of a transverse ultrasound image of a portion of an exemplary patient's limb with a suction force applied to a skin surface.

FIG. 10A is an illustration of a sonogram image produced from an ultrasound examination of the right radial artery 193 in a transverse orientation (i.e., a cross-sectional view). The artery 193 is shown in a natural state whereby the arterial lumen 197 is fully perfused with blood, prior to a proximally directed, or upward, force being applied to the skin surface 191. It can be seen from the illustration that the cross-sectional geometry of the arterial lumen 197 is substantially round and the artery 193 is at a depth $D_1$ below the skin surface 191.

FIG. 10B is an illustration of a sonogram image produced from an ultrasound examination of the right radial artery 193 in a transverse orientation (i.e., a cross-sectional view). The artery 193 is shown in a state where a proximally directed, or upward, force has been applied to the skin surface 191 directly overlying the artery 193. It can be seen from the illustration that the subcutaneous tissue 192 directly overlying the artery 193 has been substantially compressed and the depth $D_2$ of the artery 193 is less than the depth $D_1$ in FIG. 9A. It can further be seen from the image of the arterial lumen 197 that the cross-sectional geometry of the arterial lumen 197 remains substantially round under the application of upward force, i.e., the application of upward force applied to the skin surface 191 directly overlying the artery 193 has had no effect on the artery's perfusion state, nor has the artery 193 been flattened, or compressed, to be altered in shape from its natural state.

Figure 11:
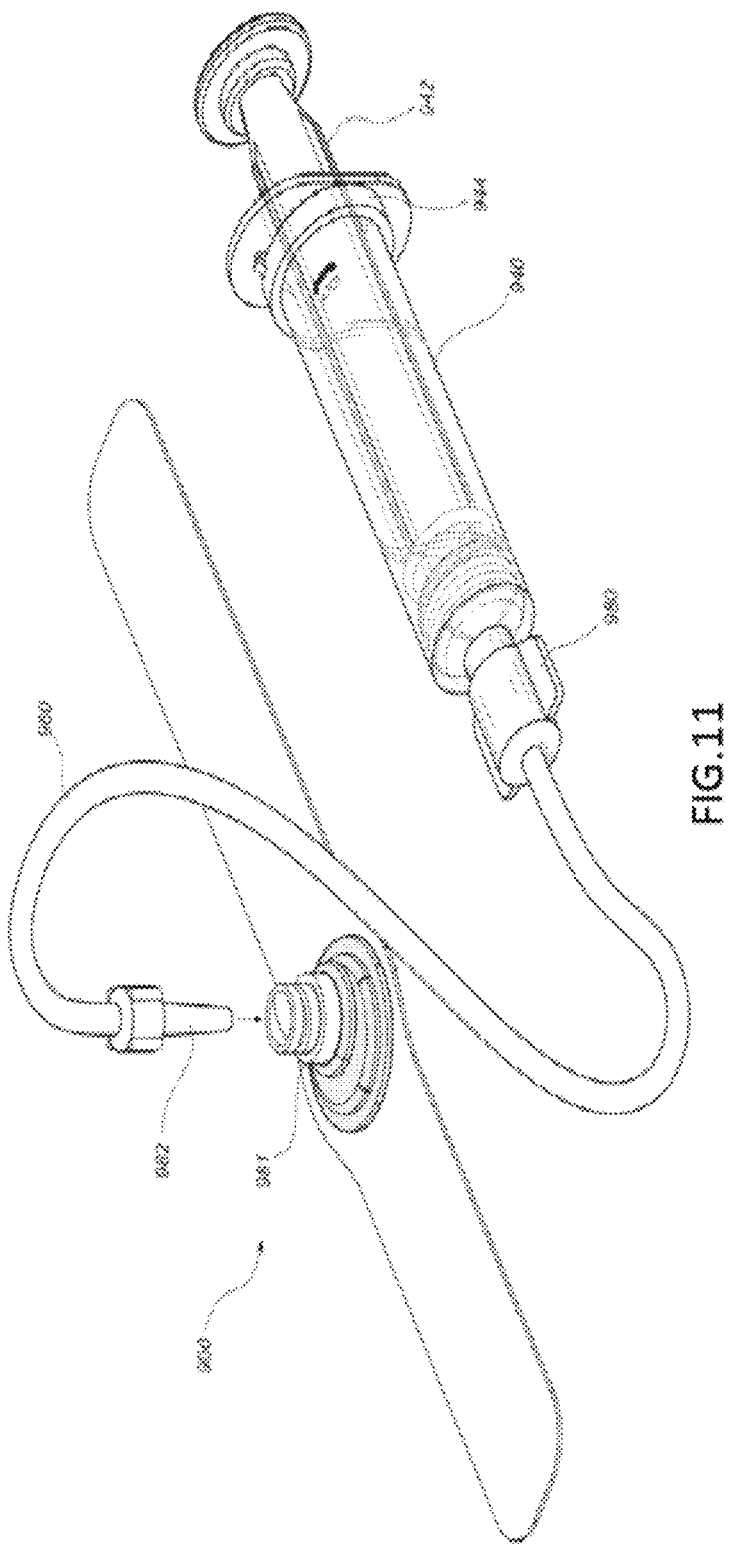
FIG. 11 shows a perspective view of an embodiment of an arteriotomy closure device of the present disclosure as a kit.

FIG. 11 depicts a kit or system that may be used to provide hemostasis at an arteriotomy following a vascular access procedure. The system or kit may include an arteriotomy closure device 900, an extension tubing member 960, and a suction generating member (e.g., syringe) 940. The arteriotomy closure device 900 may be any one of the previously described embodiments of an arteriotomy closure device. The extension tubing member 960 may include a distal fitting 982 having a distally extending protuberance configured to access a check-valve 981 of the arteriotomy closure device 900. The distal fitting 982 may be configured to access the check-valve 981 using a straight distal displacement such that a lateral force is not applied to the check-valve 981 causing the arteriotomy closure device 900 to break an airtight seal at the skin surface of the patient. The extension tubing member 960 may include a valve member 980 coupled to a proximal end. In other embodiments, the extension tubing member 960 may include a female luer fitting coupled to the proximal end. The syringe 940 is configured to couple with the proximal end of the extension tubing member 960 such that the syringe 940 is in fluid communication with the arteriotomy closure device 900 when the check-valve 981 is accessed by the distal fitting 982. A negative gauge pressure or suction force may be formed within the syringe 940 when a plunger 942 is displaced proximally. The plunger 942 may be maintained proximally displaced by an optional plunger locking member 944.

Figure 12:
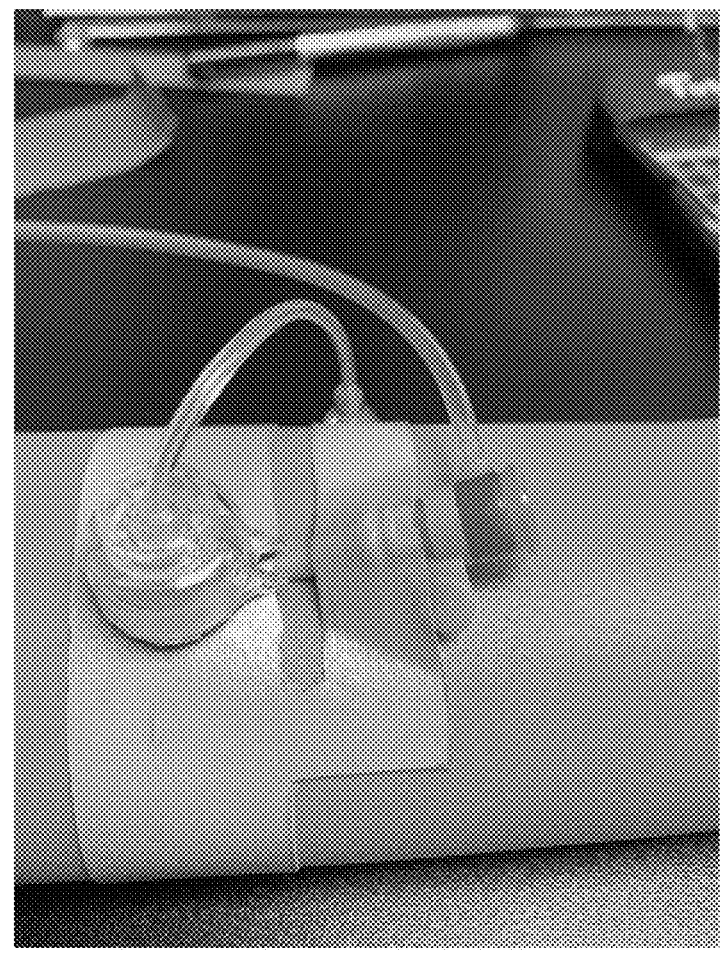
FIG. 12 shows a top perspective view of a portion of the arteriotomy closure device of FIG. 11 in an environment where it has been applied to a simulated wrist of a patient and where a percutaneous sheath has been inserted.

FIG. 12 depicts a simulated wrist with a percutaneous sheath inserted coincident with one or more alignment notches in the device. It is common practice in most catheterization labs to cover and secure the radial sheath in place. In many routine cases a clear plastic film (e.g. Tegaderm) suffices to hold the sheath in place. In some cases, however, blood leaks from the sheath valve under the plastic film and fixation is lost. In the embodiment shown, an optional secondary extension of the securement band is shown. This feature may be used for securement of a sheath. In such an embodiment, the device may be applied to a patient's skin immediately after the sheath has been inserted. The secondary extension, or sheath securement arm, of the adhesive band is placed and secured, such as by pressing firmly, over the sheath valve, thus at least partially resisting migration of the sheath during the procedure. Owing to the aggressive adhesive and the firm connection to both the sheath and the patient's skin that may optionally be used, the connection may remain intact, even in cases where blood may pool on and around the sheath valve. This embodiment also makes the securement of the sheath simpler without the need for ancillary tapes or dressings.

Figure 13A:
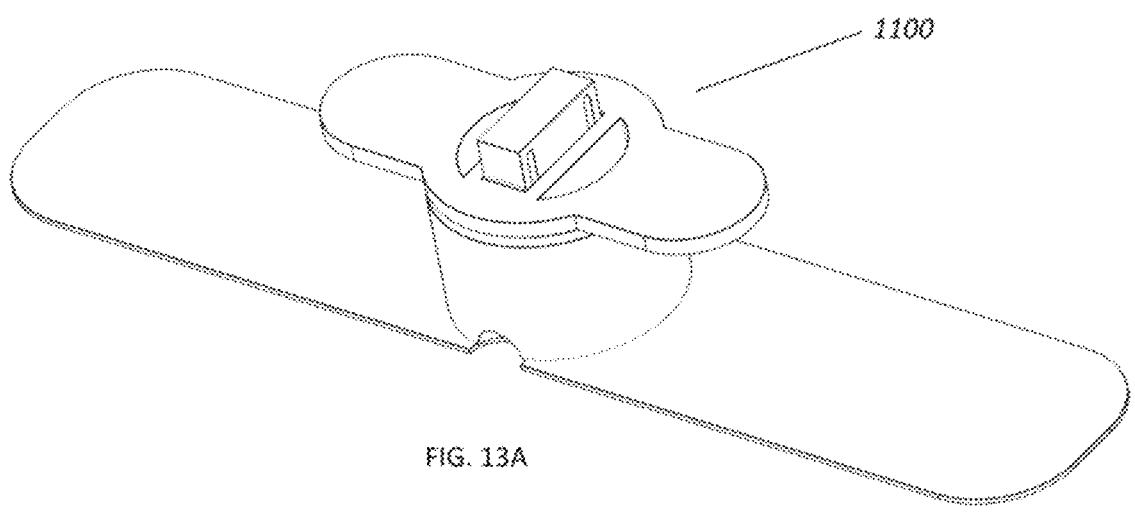
FIG. 13A shows a top perspective view of an embodiment of an arteriotomy closure device of the present disclosure in a default, or un-deployed, condition.

The embodiment shown in FIG. 13A represents a push/pull apparatus (an arteriotomy closure device) 1100 that acts much like the previous embodiments to apply external forces to the skin of a patient and close an arteriotomy; however, instead of using suction to create the external forces (i.e. push and pull forces), on the patient's limb, it utilizes mechanical energy to provide the external forces on the limb of a patient. FIG. 13A shows an embodiment of an arteriotomy closure device 1100 wherein upward positive displacement of the skin, subcutaneous tissue, and artery are facilitated by means of the application of mechanical pulling force on the surface of a patient's skin overlying an arteriotomy. The apparatus also provides a simultaneous pushing, or compressive, counterforce applied to the surface of a patient's skin overlying an arteriotomy to induce hemostasis at an arteriotomy site.

Figure 13B:
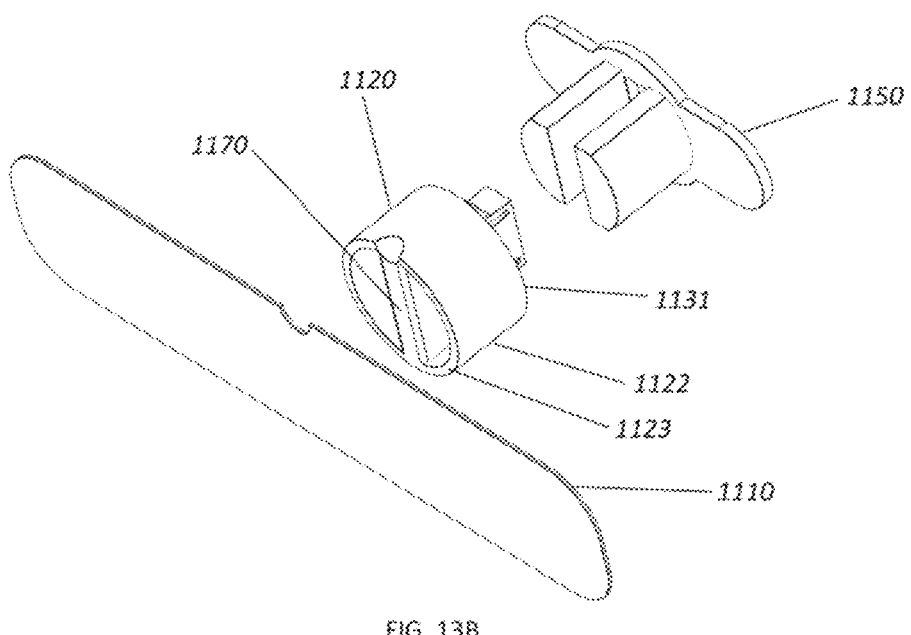
FIG. 13B shows a bottom perspective exploded view of the embodiment of the arteriotomy closure device of FIG. 13A.

The arteriotomy closure device 1100 shown in the exploded view FIG. 13B includes a housing 1120 with an integral anvil 1170, a yoke 1150, and a securement band 1110. The housing 1120 may have a generally round shape and may be formed from a material that is sufficiently rigid to apply a distally directed counterforce necessary to resist the equal and opposite force generated on the securement band by the pulling force exerted on the yoke 1150 when it is deployed proximally, or upward. For example, in the embodiment, the housing 1120 may be formed from a rigid or semi-rigid material, such as polycarbonate, high density polyurethane, polypropylene, etc. The housing 1120 can be formed using any suitable manufacturing technique, such as injection molding, casting, 3-D printing, etc. The housing may be transparent or translucent to allow a user to view the inside of the housing 1120.

The housing 1120, as illustrated in the depicted embodiment of FIG. 13B, includes a side wall 1122 extending distally from a top surface 1131. The side wall terminates at a distal surface 1123. The housing 1120 and its distal surface 1123 may consist of flat features, including a central anvil 1170 to effectively apply a counterforce to the proximal surface of a securement band 1110 and concomitantly apply a counterforce to the skin, subcutaneous tissue, and the artery.

The anvil 1170 is shown in the illustrated embodiment of FIG. 13B is disposed within the housing 1120. The anvil 1170 can divide the housing 1120 into at least two portions. The anvil 1170 includes a distal end 1171 which is flush with the distal surface 1123 of the housing 1120. In other embodiments, the distal end 1171 may be recessed into the housing 1120 or alternatively, extend beyond the distal end of the housing 1120. The anvil 1170 may be integral with the housing 1120 and formed from the same material as the housing 1120. In other embodiments, the anvil may be a separate component of a different material and coupled to the housing 1120 using any suitable technique, such as over molding, gluing, bonding, etc. In certain embodiments, the anvil 1170 may be flexible. In other embodiments, the anvil 1170 may be rigid or semi-rigid.

The anvil 1170 may be of any suitable shape such that it provides a stable downward counterforce against the patient's skin, subcutaneous tissue and artery when the arteriotomy closure device 1100 is deployed. Such anvil shapes may include a cross pattern, a substantially curved, or convex, distal end 1171. The anvil 1170 can also be configured as a central cylindrical boss with a flat distal end 1171 or a central cylindrical anvil with a substantially smooth radiused distal end 1171, for example. Such examples of anvil shapes are depicted supra in FIGS. 2A-5B.

Figure 13C:
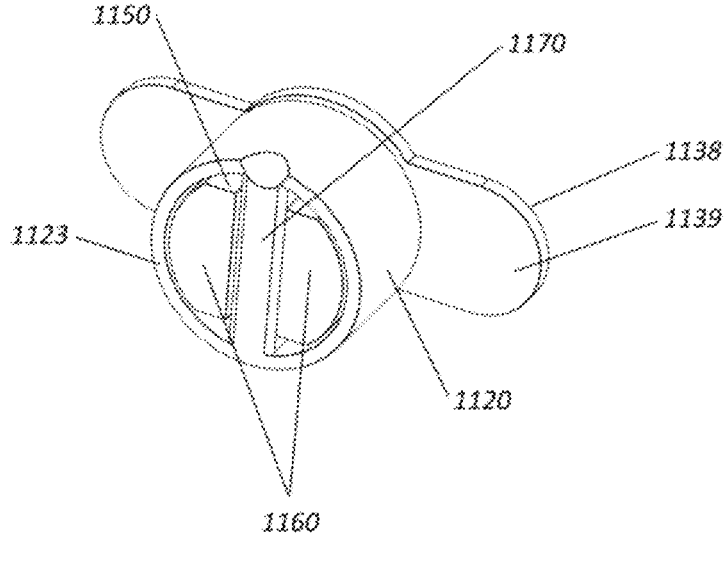
FIG. 13C shows a partial bottom perspective view of components of the embodiment of the the arteriotomy closure device of FIG. 13A.

Referring to FIG. 13C, the arteriotomy closure device is shown where the yoke 1150 has been inserted into the housing 1120 such that its distal surface 1151 has protruded beyond the distal surface 1123 of the housing 1120, i.e. the default, or pre-deployed, condition.

As depicted in FIG. 13C, the yoke is comprised of two crescent-shaped, or semi crescent-shaped, lobes 1160 which are slide-ably located on either side of the central anvil 1170 of the housing 1120 and connected at their proximal margin to an upper plate 1138. The yoke 1150 may be formed from a rigid or semi-rigid material, such as polycarbonate, high density polyurethane, polypropylene, etc. The yoke 1150 can be formed using any suitable manufacturing technique, such as injection molding, casting, 3-D printing, etc. The yoke 1150 may be transparent or translucent to allow the user to visualize the yoke 1150.

As shown in FIG. 13C, in the un-deployed, or default, condition, the proximal margin 1131 of the housing 1120 is in close proximity with the distal surface 1139 of the upper plate 1138 of the yoke 1150. In this condition, the distal-most surfaces of the yoke extend beyond the distal surface 1123 of the housing 1120.

Figure 13D:
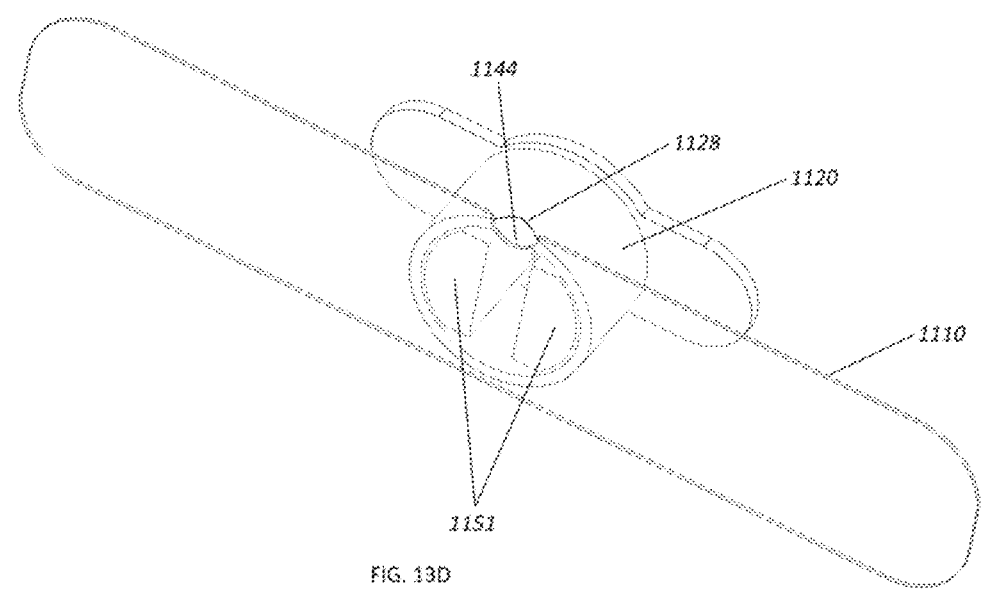
FIG. 13D shows a partially transparent bottom perspective view of the embodiment of the arteriotomy closure device of FIG. 13A.

As shown in FIG. 13D, the yoke 1150, when fully inserted in the housing 1120 may be adhesively coupled to the proximal surface of a securement band 1110 (shown as transparent) via adhesive applied to the distal surface 1151 of the yoke 1150. The yoke 1150 may be attached, such as by pressing, through creating contact, or through the application of force, to the top surface of the securement band. In the embodiment shown, the yoke 1150 is attached to the securement band 1110 such that the notch 1128 on the housing 1120 aligns with a complimentary notch 1144 on the securement band 1110. The resulting connection between the housing 1120 and the securement band 1110 may be substantially strong to resist separation during the deployment and use when the arteriotomy closure device 1100 is applied to the limb of a patient.

The securement band 1110 may be configured to be disposed around a portion of a patient's limb in order to secure the arteriotomy closure device 1100 over an arteriotomy site. For example, the securement band 1110 may be a wrist band configured to be disposed around a wrist of a patient such that the device 1100 can be secured over a radial, ulnar or palmar artery arteriotomy site. In other embodiments, the securement band 110 may be configured to be disposed around a patient's hand, thigh, ankle, upper arm, etc. In some embodiments the palmar artery may be accessed at the anatomical snuffbox of the patient. The securement band 1110 may be formed of a flexible, low modulus/low durometer polymeric membrane and include a "peel and stick" distal surface 1112 to be adhesively fixed to the skin when disposed around a portion of the patient's limb.

Figure 13E:
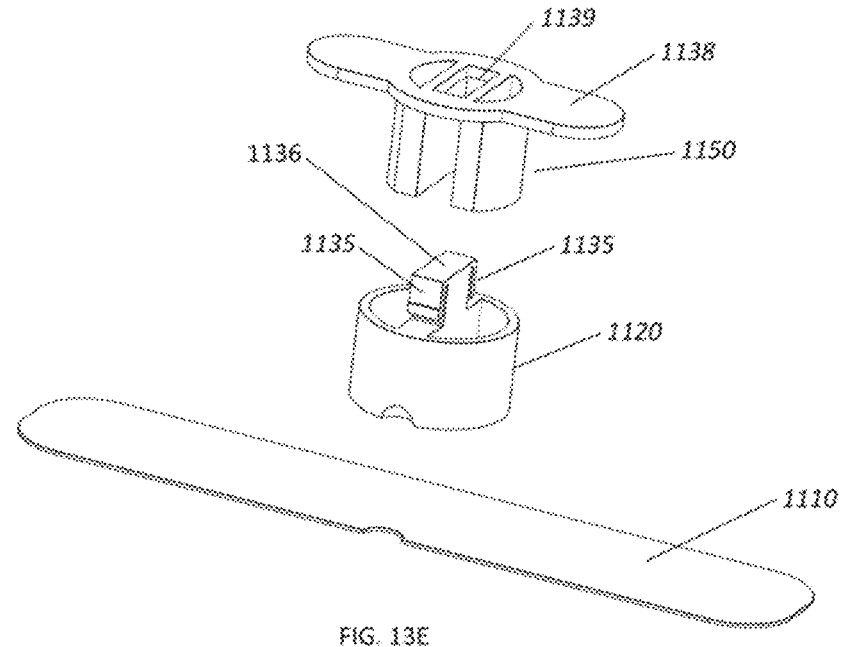
FIG. 13E shows a top perspective exploded view of components of the embodiment of the arteriotomy closure device of FIG. 13A.
Figure 13F:
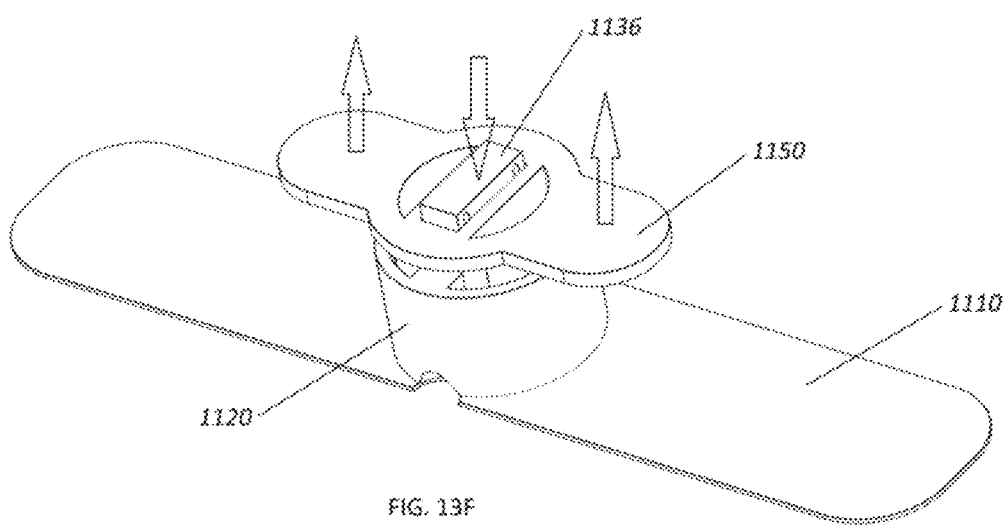
FIG. 13F shows a top perspective view of the embodiment of the arteriotomy closure device of FIG. 13A in a deployed, or locked condition.
Figure 13G:
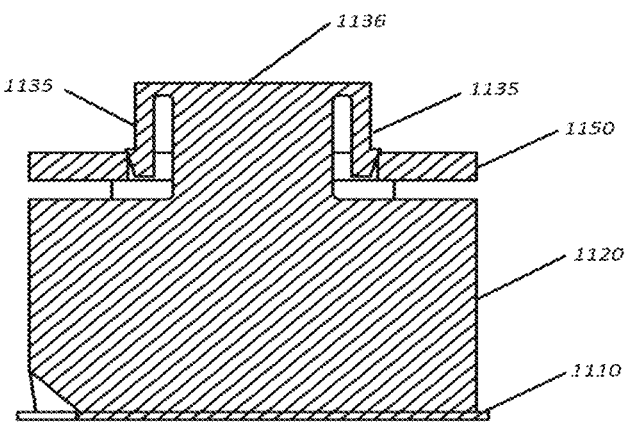
FIG. 13G shows a partial side cross-sectional view of a portion of the embodiment of the arteriotomy closure device of FIG. 13A in a default, or un-deployed, condition.
Figure 13H:
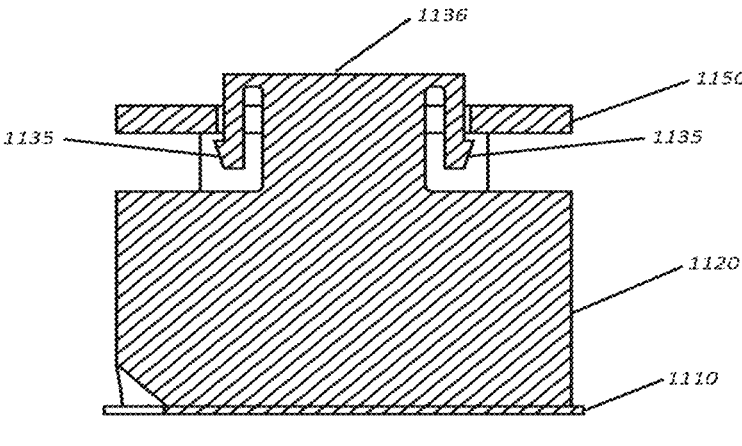
FIG. 13H shows a partial side cross-sectional view of a portion of the embodiment of the arteriotomy closure device of FIG. 13F in a deployed, or locked, condition.

Referring to FIGS. 13E-13F, the housing 1120 has a proximal margin which includes two snap fingers 1135 and a top surface 1136 (i.e. a thumb pad) which when pressed in a distal direction while simultaneously pulling the yoke 1150 in a proximal direction, the snap fingers 1135 of the housing 1120 are relocated in a snapped, or deployed, position at the distal margin 1139 of the upper plate 1138 of the yoke 1150, thus locking the yoke 1150 in its proximal deployed position relative to the housing 1120. FIG. 13F shows the arteriotomy closure device 1100 in a fully deployed, or locked, configuration with arrows indicating the relative displacements of the yoke 1150 and the housing 1120. Additionally, FIGS. 13 G and 13 H show the snap fingers 1135 in the default position and in the fully deployed position respectively.

In use, following an arterial catheterization procedure and prior to removal of an introducer sheath, the arteriotomy closure device 1100 may be positioned on a portion of a limb of a patient such that it is disposed over an arteriotomy site. In certain embodiments, the arteriotomy closure device 1100 may be disposed over the arteriotomy site, a skin puncture site, and/or a tissue tract between the arteriotomy site and the skin puncture site. The securement band 1110 may be wrapped around the portion of the limb with its distal surface 1112 positioned to be adhesively connected to the patient's skin. The securement band 1110 may be held tightly to the patient's skin such that its distal surface 1112 provides a proximally directed pulling force on the patient's skin when the yoke 1150 is deployed in a proximal direction relative to the housing 1120. The proximal displacement of the distal surface 1151 of the yoke (not shown) 1150 may cause the securement band to be drawn, or distended, in a proximal, or puckered, position while simultaneously, the distal margin 1123 (not shown) of the housing 1120 along with the distal margin 1171 (not shown) of the anvil 1170 (not shown) are displaced in a distal direction, thus creating a simultaneous pull force and push force respectively. By way of the adhesive attachment of the securement band to the patient's skin, the skin, subcutaneous tissue and artery are likewise drawn, or distended, in a proximal, or puckered, position while simultaneously, the distal margin 1171 of the anvil 1170 and the distal margin 1123 of the housing 1120 apply a counter force against the patient's skin overlying the arteriotomy and/or a tissue tract which facilitates hemostasis, or cessation of bleeding, from the arteriotomy. In certain embodiments, the deployment sequence may be executed prior to removal of the introducer sheath from the artery. In other embodiments, the introducer sheath is removed from the artery prior to the deployment sequence.

Figure 13I:
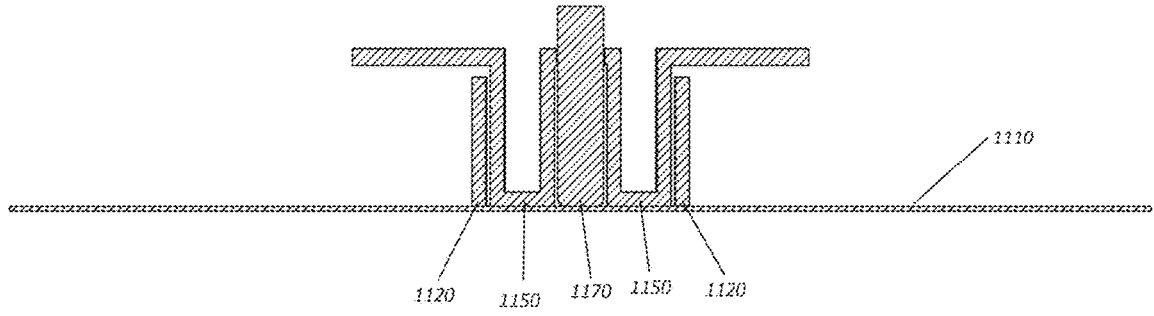
FIG. 13I shows a partial cross-sectional view of a portion of the embodiment of the arteriotomy closure device of FIG. 13A in a default, or un-deployed, condition.
Figure 13J:
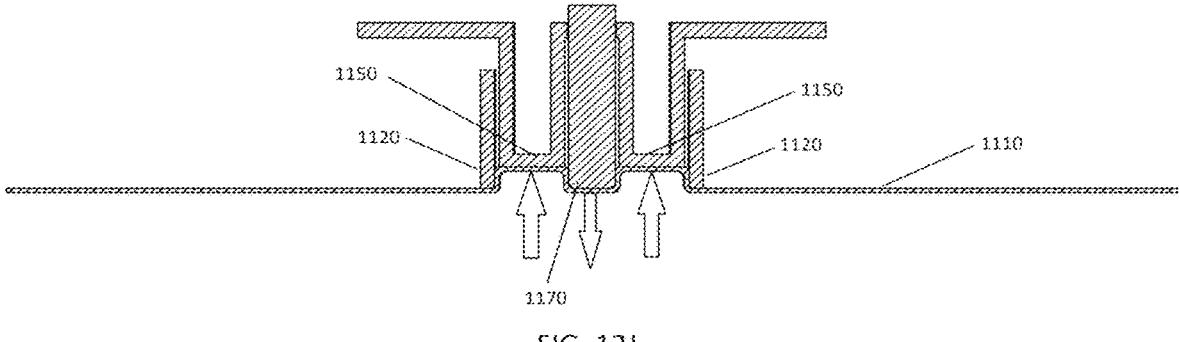
FIG. 13J shows a partial cross-sectional view of a portion of the embodiment of the arteriotomy closure device of FIG. 13F in a deployed, or locked, condition.

FIGS. 13I and 13J depict cross-sectional views of the housing 1120, the anvil 1170, and the yoke 1150 in the default condition and the fully deployed condition respectively. In FIG. 13J, arrows are shown indicating the relative displacements of the components.

When cessation of bleeding from the skin puncture site has been achieved after a set period of time, the arteriotomy closure device 1100 may be removed from the patient's limb.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention. Accordingly, various modifications, adaptations, combinations, and alternatives may occur to one skilled in the art without departing from the spirit of the invention and scope of the claimed coverage.

What is claimed is:

1. An arteriotomy closure device, comprising:
a housing defining a first at least partially open suction volume and having a first bottom surface;
a force application feature comprising a fluid displacement member which is further configured to selectively induce negative gauge pressure;
a securement band having a first top surface and a second bottom surface and defining a gas-impermeable membrane; and
an anvil at least partially disposed within the first at least partially open suction volume and comprising a third bottom surface;
wherein the securement band further comprises an adhesive feature which at least partially aids in retaining at least a portion of the second bottom surface to a patient's skin, and further wherein the fluid displacement member is in fluid communication with the first at least partially open suction volume, and further wherein at least a first portion of the first top surface is in contact with the third bottom surface when the arteriotomy closure device is transitioned from an undeployed configuration to a deployed configuration.

2. The arteriotomy closure device of claim 1, further wherein the gas-impermeable membrane is configured to define an airtight seal between the at least partially open suction volume and the patient's skin.

3. The arteriotomy closure device of claim 2, further comprising a valve in fluid communication with the first at least partially open suction volume and configured to selectively retain a negative gauge pressure within the first at least partially open suction volume.

4. The arteriotomy closure device of claim 1, further wherein the force application feature is a syringe.

5. The arteriotomy closure device of claim 1, further wherein the force application feature is a vacuum pump.

6. The arteriotomy closure device of claim 1, further wherein the first bottom surface is configured to create an airtight seal against at least a second portion of the first top surface.

7. The arteriotomy closure device of claim 1, further comprising at least one window configured to permit a user to visualize at least a second portion of the first top surface within the at least partially open suction volume and proximal to the anvil.

8. The arteriotomy closure device of claim 1, further wherein the adhesive feature is at least partially below the at least partially open suction volume relative to the first bottom surface, and further wherein the adhesive feature is configured to retain an exterior surface of skin of a patient when a negative gauge pressure is applied to the at least partially open suction volume.

9. The arteriotomy closure device of claim 1, further wherein the third bottom surface is configured to apply pressure to a patient's skin, subcutaneous tissue, and artery through the securement band when the arteriotomy closure device is in the deployed configuration.

10. An arteriotomy closure device, comprising:

a housing defining a first at least partially open suction volume, having a first bottom surface, and comprising an inner wall which is at least partially defined by the first at least partially open volume;

a suction assembly comprising a syringe;

a valve;

a securement band having a first top surface and a second bottom surface and defining a gas-impermeable membrane; and an anvil at least partially disposed within the first at least partially open suction volume, connected to the inner wall, and comprising a third bottom surface;

wherein the first bottom surface is connected to the first top surface through an adhesive bond, the adhesive bond is an airtight connection, the securement band further comprises a peel-and-stick feature which at least partially aids in retaining at least a first portion of the second bottom surface beneath the at least partially open suction volume relative to the first bottom surface to a patient's skin, and wherein the syringe is in fluid communication with the first at least partially open suction volume and with the valve, and further wherein at least a first pressure portion of the third bottom surface is in contact with at least a second portion of the first top surface above an arteriotomy site when the arteriotomy closure device is transitioned from an undeployed configuration to a deployed configuration, and further wherein the at least a first portion of the second bottom surface and a flexural region of the securement band above the at least a first portion of the second bottom surface relative to the first bottom surface is flexibly deformable.

\* \* \* \* \*